US012677120B2

(12) United States Patent
He

(10) Patent No.: US 12,677,120 B2
(45) Date of Patent: Jul. 7, 2026

(54) APPARATUSES, COMPUTER-IMPLEMENTED METHODS, AND COMPUTER PROGRAM PRODUCTS FOR CLEAR AIR TURBULENCE DETECTION

(71) Applicant: Honeywell International Inc, Charlotte, NC (US)

(72) Inventor: Ye He, Shanghai (CN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 18/610,449

(22) Filed: Mar. 20, 2024

(65) Prior Publication Data

US 2025/0301291 A1     Sep. 25, 2025

(51) Int. Cl.
| | |
|---|---|
| *H04W 4/46* | (2018.01) |
| *A61B 5/0205* | (2006.01) |
| *A61B 5/08* | (2006.01) |
| *A61B 5/145* | (2006.01) |
| *B60W 50/04* | (2006.01) |

(Continued)

(52) U.S. Cl.
CPC ........... *H04W 4/46* (2018.02); *A61B 5/02055* (2013.01); *A61B 5/0816* (2013.01); *A61B 5/14542* (2013.01); *B60W 50/045* (2013.01); *G01W 1/10* (2013.01); *G06F 3/013* (2013.01); *H04W 4/02* (2013.01); *G01W 2001/003* (2013.01)

(58) Field of Classification Search
CPC ...... H04W 4/46; H04W 4/02; A61B 5/02055; A61B 5/0816; A61B 5/14542; B60W 50/045; G01W 1/10; G01W 2001/003; G06F 3/013

USPC .......................................................... 701/14
See application file for complete search history.

(56) References Cited

U.S. PATENT DOCUMENTS

| | | | |
|---|---|---|---|
| 8,209,071 B2 | 6/2012 | Ross | |
| 9,881,507 B2 | 1/2018 | Rencher et al. | |

(Continued)

FOREIGN PATENT DOCUMENTS

| | | |
|---|---|---|
| EP | 4246096 A1 | 9/2023 |
| WO | 2018/011791 A2 | 1/2018 |

OTHER PUBLICATIONS

Extended European Search Report Mailed on Aug. 22, 2025 for EP Application No. 25159587, 10 page(s).

*Primary Examiner* — Krishnan Ramesh
(74) *Attorney, Agent, or Firm* — ALSTON & BIRD LLP

(57)     ABSTRACT

Embodiments of the disclosure provide for clear air turbulence (CAT) detection. In the context of a method, the method includes receiving, from a vehicle, biometric data for at least one subject aboard the vehicle, wherein the biometric data meets a biometric abnormality threshold; applying a first weight value to a first subset of the biometric data determined to correspond to a passenger aboard the vehicle; applying a second weight value to a second subset of the biometric data determined to correspond to a crew-member aboard the vehicle, wherein the first weight value represents a greater impact value than the second weight value; determining the vehicle has encountered a monitored vehicle event representing CAT based at least in part on the first and second weight values; generating a predicted event location based on vehicle data associated with the vehicle; and providing the predicted event location to an additional vehicle.

20 Claims, 5 Drawing Sheets

(51) Int. Cl.
    G01W 1/00          (2006.01)
    G01W 1/10          (2006.01)
    G06F 3/01          (2006.01)
    H04W 4/02          (2018.01)

(56)                    References Cited

U.S. PATENT DOCUMENTS

| | | | |
|---|---|---|---|
| 11,192,664 B2 * | 12/2021 | Ramaswamy | ........... G08G 5/20 |
| 11,987,379 B2 * | 5/2024 | Rowan | .................. G06F 3/0484 |
| 2014/0106333 A1 * | 4/2014 | Dugan | ................ G07C 5/0825 |
| | | | 340/978 |
| 2016/0133137 A1 | 5/2016 | Rencher et al. | |
| 2018/0234707 A1 * | 8/2018 | Pujia | ................. H04N 21/4227 |
| 2020/0180790 A1 * | 6/2020 | Ramaswamy | ........... G08G 5/21 |
| 2020/0401934 A1 | 12/2020 | Trim et al. | |
| 2023/0030733 A1 * | 2/2023 | Rowan | .................. B64D 45/00 |

* cited by examiner

500

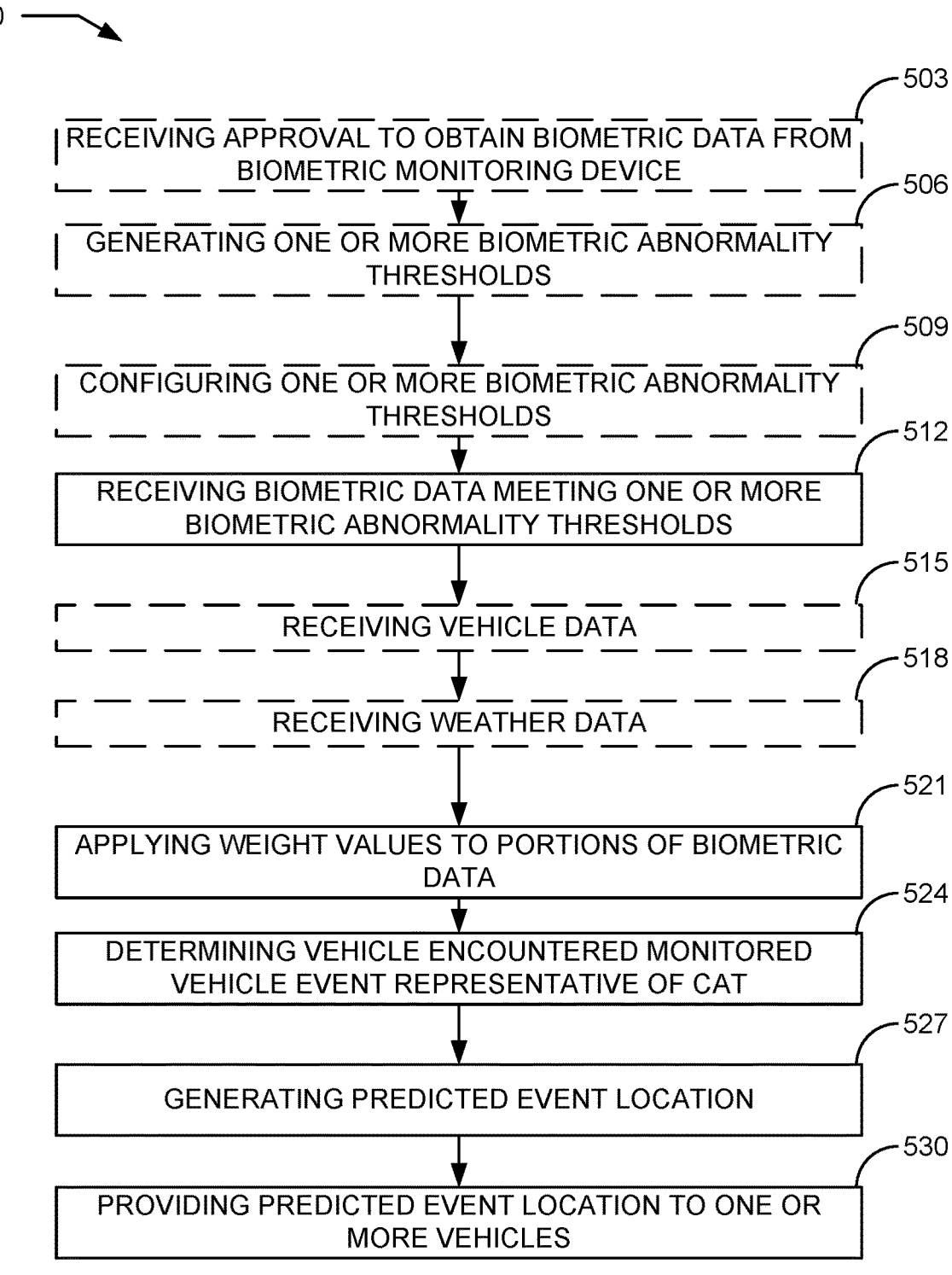

503
RECEIVING APPROVAL TO OBTAIN BIOMETRIC DATA FROM BIOMETRIC MONITORING DEVICE

506
GENERATING ONE OR MORE BIOMETRIC ABNORMALITY THRESHOLDS

509
CONFIGURING ONE OR MORE BIOMETRIC ABNORMALITY THRESHOLDS

512
RECEIVING BIOMETRIC DATA MEETING ONE OR MORE BIOMETRIC ABNORMALITY THRESHOLDS

515
RECEIVING VEHICLE DATA

518
RECEIVING WEATHER DATA

521
APPLYING WEIGHT VALUES TO PORTIONS OF BIOMETRIC DATA

524
DETERMINING VEHICLE ENCOUNTERED MONITORED VEHICLE EVENT REPRESENTATIVE OF CAT

527
GENERATING PREDICTED EVENT LOCATION

530
PROVIDING PREDICTED EVENT LOCATION TO ONE OR MORE VEHICLES

FIG. 5

APPARATUSES, COMPUTER-IMPLEMENTED METHODS, AND COMPUTER PROGRAM PRODUCTS FOR CLEAR AIR TURBULENCE DETECTION

TECHNOLOGICAL FIELD

Embodiments of the present disclosure are generally directed to enhancing detection of clear air turbulence (CAT).

BACKGROUND

Typical approaches to detecting areas of CAT rely upon weather forecast reports or flight downlink data. For example, a weather forecast may indicate that conditions in an area are appropriate for causing CAT. However, weather forecasts commonly lag current conditions by 6 hours or greater and, therefore, may demonstrate insufficient accuracy for predicting whether a vehicle will experience CAT. As another example, a pilot report (PIREP) may include a turbulence record portion in which CAT encounters are documented by the pilot. Typically, downlink of the PIREP must be manually initiated by the pilot. Therefore, CAT reporting may occur long after CAT is experienced, if at all, depending on when the PIREP is broadcasted. Further the pilot's estimation of CAT severity may be based on subjective, generalized categories (e.g., unknown, none, light, moderate, severe extreme). In another example, onboard calculations that are performed to detect and register a CAT event may lag CAT occurrence and, as a result, estimations of CAT location may be imprecise due to latencies in performing the calculations.

Applicant has discovered various technical problems associated with accurately detecting CAT events and locations. Through applied effort, ingenuity, and innovation, Applicant has solved many of these identified problems by developing the embodiments of the present disclosure, which are described in detail below.

BRIEF SUMMARY

In general, embodiments of the present disclosure herein provide for detection of vehicle events representing clear air turbulence (CAT) based at least in part on biometric data associated with one or more subjects aboard a vehicle. For example, embodiments of the present disclosure provide for receiving real-time biometric data from a subject aboard a vehicle, determining the biometric data meets a biometric abnormality threshold for the subject, and, in response, determining the vehicle has encountered a monitored vehicle event representing CAT. Further, embodiments of the present disclosure provide for determining a predicted event location of the CAT based at least in part on vehicle data associated with the vehicle. For example, the predicted event location may be determined based at least in part on a location of the vehicle during an interval where the biometric data for the subject exceeded the biometric abnormality threshold. Various embodiments of the present disclosure further provide for provisioning the predicted event location to one or more additional vehicles. In doing so, the present method, apparatus, and computer program product may overcome technical challenges associated with detecting and communicating locations of CAT in substantially real-time as compared to existing approaches where CAT detection demonstrates several hours of lag. Other implementations for detecting monitored vehicle events based on biometric data will be, or will become, apparent to one with skill in the art upon examination of the following figures and detailed description. It is intended that all such additional implementations be included within this description be within the scope of the disclosure, and be protected by the following claims.

In accordance with a first aspect of the disclosure, a computer-implemented method for detecting a monitored vehicle representing CAT is provided. The computer-implemented method is executable utilizing any of a myriad of computing device(s) and/or combinations of hardware, software, firmware. In some example embodiments an example computer-implemented method includes receiving, from a vehicle, real-time biometric data for at least one subject aboard the vehicle, wherein the real-time biometric data meets at least one biometric abnormality threshold; applying a first weight value to at least a first subset of the real-time biometric data determined to correspond to at least one passenger aboard the vehicle; applying a second weight value to at least a second subset of the real-time biometric data determined to correspond to at least one crewmember aboard the vehicle, wherein the first weight value represents a greater impact value than the second weight value; determining the vehicle has encountered a monitored vehicle event representing clear air turbulence (CAT), wherein the determination that the vehicle has encountered the monitored vehicle event is based at least in part on the first weight value and the second weight value; obtaining vehicle data associated with the vehicle; generating a predicted event location based at least in part on the vehicle data; and providing the predicted event location to at least one additional vehicle.

In some embodiments, the method further includes configuring the at least one biometric abnormality threshold on at least one of: a biometric monitoring device carried by the at least one subject aboard the vehicle; or a vehicle management system configured to receive biometric readings from at least one sensor installed within the vehicle, wherein each of the biometric monitoring device or the vehicle management system are configured to generate and analyze the real-time biometric data for the at least one subject based on the at least one biometric abnormality threshold. In some embodiments, the method includes generating the at least one biometric abnormality threshold based at least in part on historical biometric data associated with the at least one subject.

In some embodiments, the biometric data comprises at least one of heart rate, respiration rate, pulse, or blood pressure. In some embodiments, the biometric data comprises at least one voice signature. In some embodiments, the biometric data comprises eye movement frequency. In some embodiments, the biometric data comprises at least one blood oxygen level. In some embodiments, the biometric data comprises at least one timestamp for a time interval in which the biometric data met the at least one biometric abnormality threshold. In some embodiments, the vehicle data comprises at least one of a vehicle location, vehicle speed, vehicle pitch, or vehicle altitude measured within the time interval.

In some embodiments, the method includes determining the vehicle has encountered the monitored vehicle event representing CAT further based at least in part on a pilot report (PIREP) associated with the vehicle. In some embodiments, the vehicle is configured to generate the PIREP in response to the biometric data meeting the at least one biometric abnormality threshold. In some embodiments, the method includes determining the vehicle has encountered the monitored vehicle event representing CAT further based at least in part on weather data associated with a travel pathway of the vehicle.

In some embodiments, the real-time biometric data is generated by a biometric monitoring device carried by the at least one subject aboard the vehicle. In some embodiments, the method further includes provisioning to the biometric monitoring device a request to receive real-time biometric data. In some embodiments, the method includes receiving from the biometric monitoring device an approval of the request. In some embodiments, the method includes receiving eddy dissipation rate (EDR) data from the vehicle, wherein the EDR data is compensated based at least in part on a time interval associated with the real-time biometric data. In some embodiments, the at least one biometric abnormality threshold comprises: a first threshold associated with the at least one passenger; and a second threshold associated with the at least one crewmember, wherein the second threshold is greater than the first threshold.

In some embodiments, the method includes modifying at least one travel pathway based at least in part on the predicted event location. In some embodiments, the method includes providing the at least one travel pathway to the at least one additional vehicle. In some embodiments, the providing of the at least one travel pathway to the at least one additional vehicle causes the at least one additional vehicle to circumvent an area comprising the predicted event location.

In accordance with another aspect of the present disclosure, a computer program product for detecting a monitored vehicle representing CAT is provided. The computer program product in some embodiments includes at least one non-transitory computer-readable storage medium having computer program code stored thereon. The computer program code in execution with at least one processor is configured for performing any one of the example computer-implemented methods described herein.

BRIEF DESCRIPTION OF THE DRAWINGS

Figure 1:
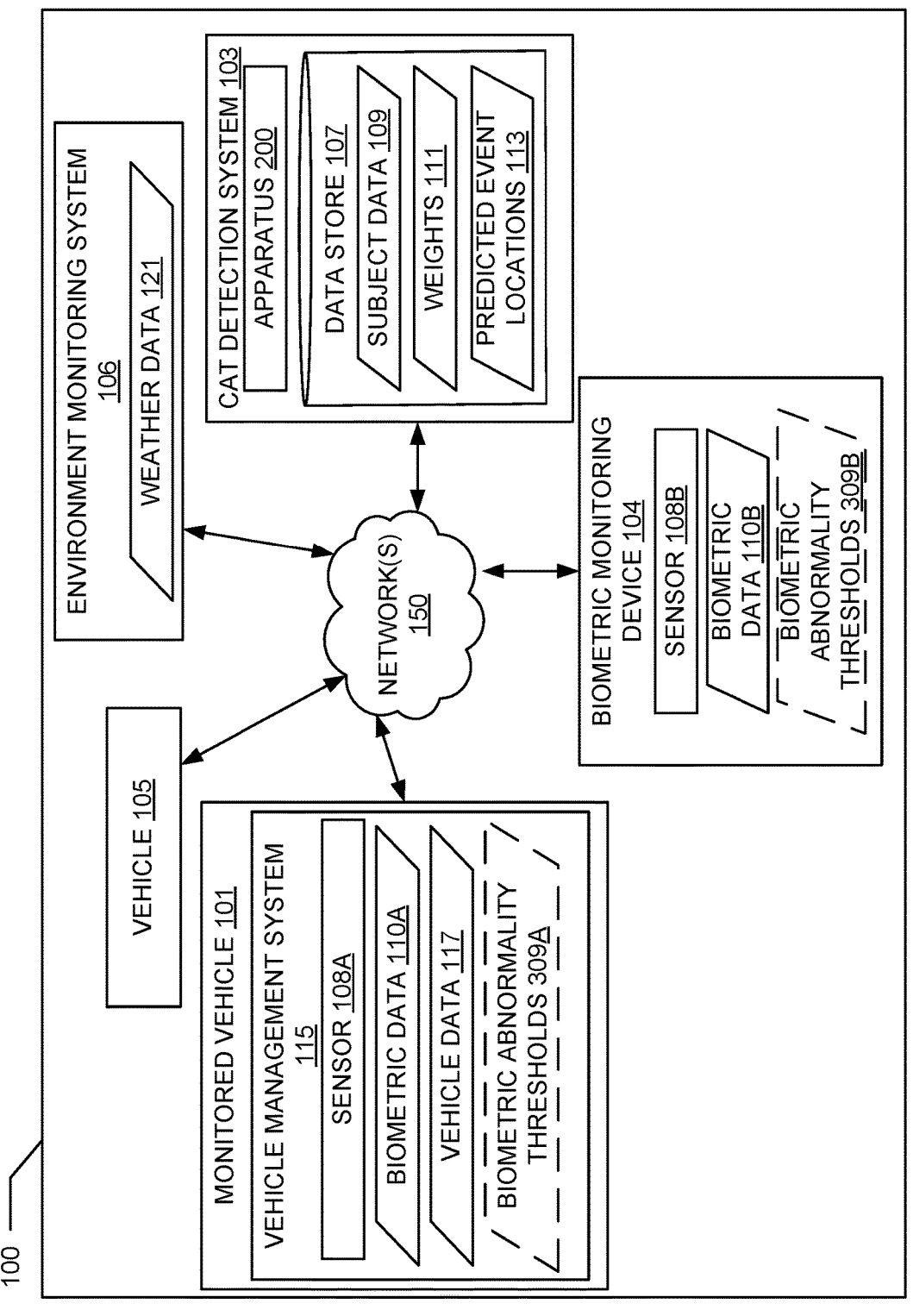

Having thus described the embodiments of the disclosure in general terms, reference now will be made to the accompanying drawings, which are not necessarily drawn to scale, and wherein:

FIG. 1 illustrates a block diagram of a networked environment that may be specially configured within which embodiments of the present disclosure may operate.

Figure 2:
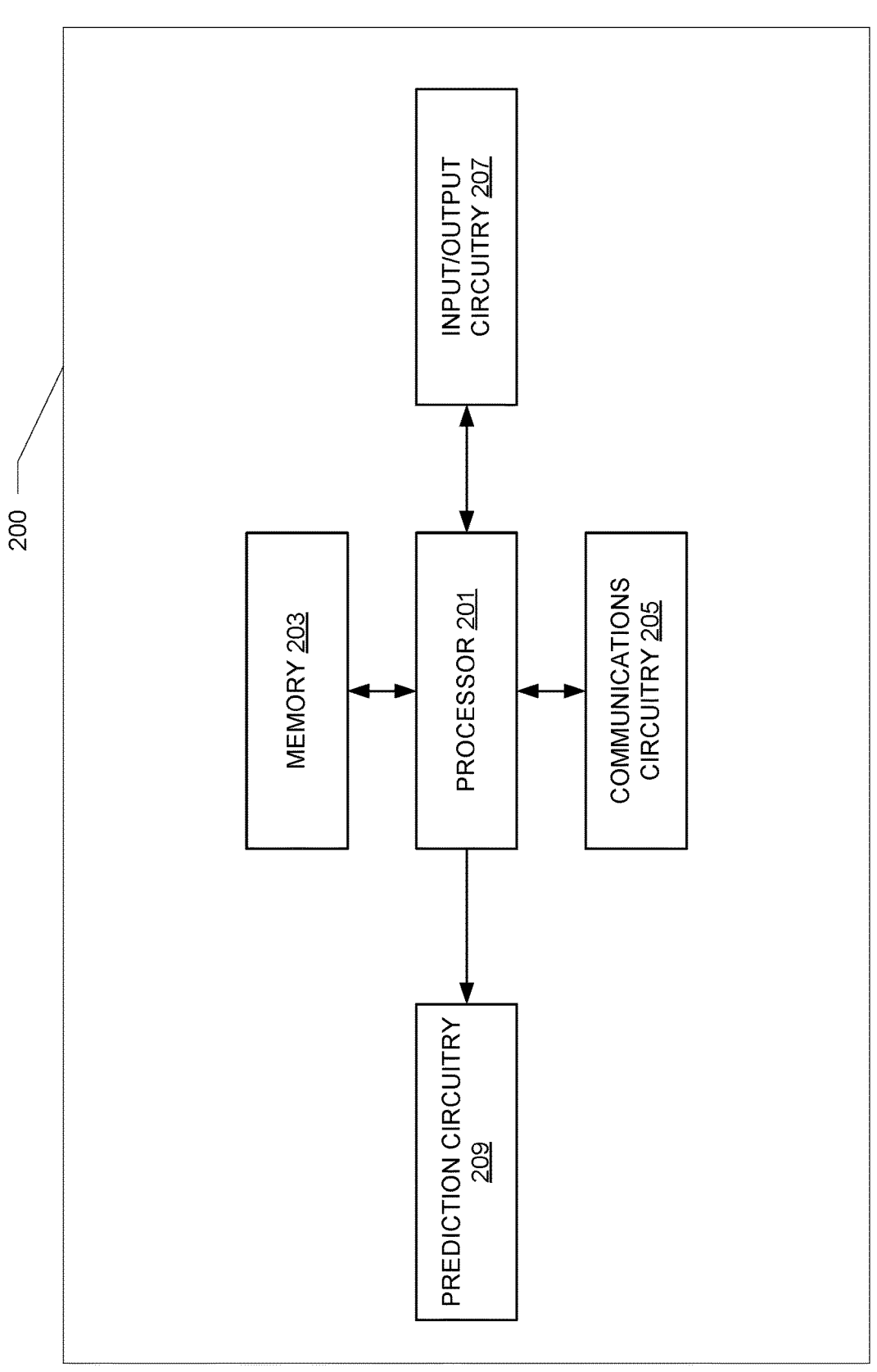

FIG. 2 illustrates a block diagram of an example apparatus that may be specially configured in accordance with at least some example embodiments of the present disclosure.

Figure 3:
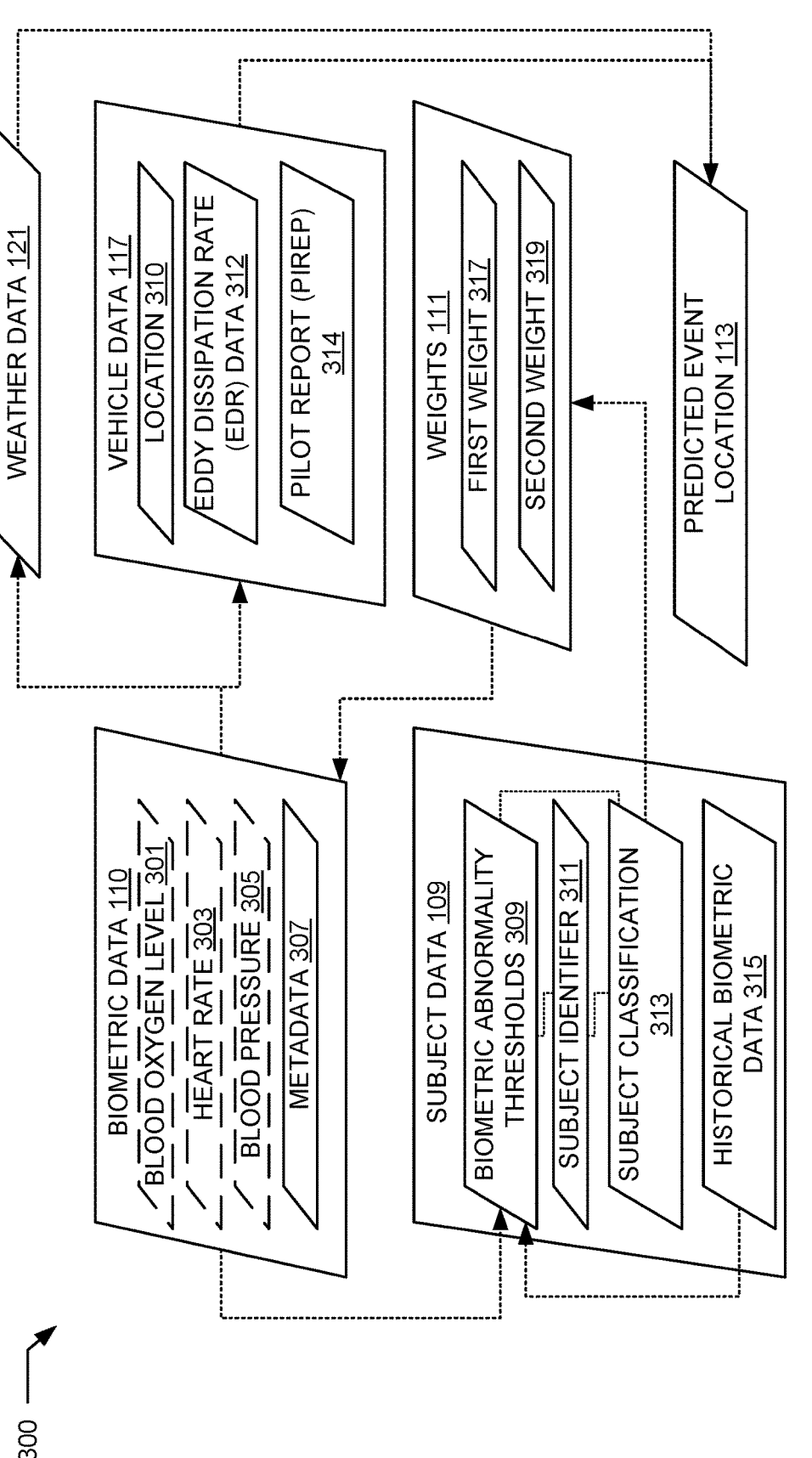

FIG. 3 illustrates an example data architecture in accordance with at least some example embodiments of the present disclosure.

Figure 4:
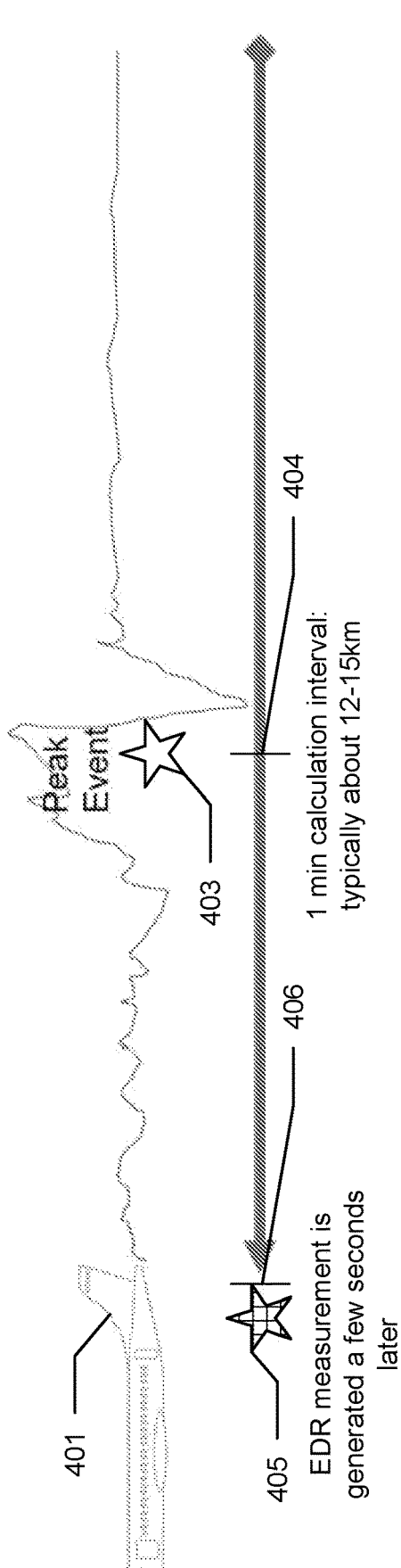

FIG. 4 illustrates an existing approach to CAT detection in an aerial context.

FIG. 5 illustrates a flowchart depicting operations of an example process for biometric-based CAT detection in accordance with at least some example embodiments of the present disclosure.

DETAILED DESCRIPTION

Embodiments of the present disclosure now will be described more fully hereinafter with reference to the accompanying drawings, in which some, but not all, embodiments of the disclosure are shown. Indeed, embodiments of the disclosure may be embodied in many different forms and should not be construed as limited to the embodiments set forth herein, rather, these embodiments are provided so that this disclosure will satisfy applicable legal requirements. Like numbers refer to like elements throughout.

OVERVIEW

Embodiments of the present disclosure provide a myriad of technical advantages in the technical field of detecting clear air turbulence (CAT). Typically, CAT is detected in a delayed manner based on a vehicle operator manually generating and downlinking a report indicative of an encounter with turbulence. For example, in an aerial context, a pilot may experience CAT during a portion of a flight path and report the CAT by preparing and submitting a pilot report (PIREP). The pilot may also initiate measurements of eddy dissipation rate (EDR) data to estimate a location of the CAT encounter. In such approaches, the latencies of report preparation and EDR data generation may result in inaccurate predictions of CAT location. For example, a vehicle may traverse tens of miles and thousands of feet between the time at which CAT is encountered, a time at which the pilot generates the PIREP, and a time at which EDR data points are measured. In addition to delayed detection and localization of CAT, such approaches are highly dependent upon the subjective observations of the pilot in determining that the vehicle has encountered CAT.

Embodiments of the present disclosure overcome the technical challenges of identifying CAT and predicting CAT location by introducing techniques that utilize biometric data of subjects aboard a vehicle to detect changes in biological responses indicative of a monitored vehicle event representing CAT. The techniques may be performed by various embodiments of methods, apparatuses, and computer program products as described herein. In various embodiments, a method, apparatus, or computer program product may automatically initiate the generation and downlink of PIREPs, EDR data, and/or the like in response to biometric data-based detection of a monitored vehicle event representing CAT. In doing so, the method, apparatus, and computer program product may improve the accuracy and precision of CAT detection and CAT location prediction. Further, the method, apparatus, or computer program product, may provide predicted event locations to additional vehicles to enable preparation for and/or avoidance of CAT. In doing so, the method, apparatus, and computer program product may enhance vehicle safety and the safety and comfort of vehicle occupants.

Definitions

"Vehicle" refers to any apparatus that traverses throughout an environment by any mean of travel. In some contexts, a vehicle transports goods, persons, and/or the like, or traverses itself throughout an environment for any other purpose, by means of air, sea, or land. In some embodiments, a vehicle is ground-based, air-based, water-based, space-based (e.g., outer space or within an orbit of a planetary body, a natural satellite, or artificial satellite), and/or the like. In some embodiments, the vehicle is an aerial vehicle capable of air travel. Non-limiting examples of aerial vehicles include urban air mobility vehicles, drones, helicopters, fully autonomous air vehicles, semi-autonomous air vehicles, airplanes, orbital craft, spacecraft, and/or the like. In some embodiments, the vehicle is piloted by a human operator onboard the vehicle. For example, in an aerial context, the vehicle may be a commercial airliner operated by a flight crew. In some embodiments, the vehicle is remotely controllable such that a remote operator may initiate and direct movement of the vehicle. Additionally, in some embodiments, the vehicle is unmanned. For example, the vehicle may be a powered, aerial vehicle that does not carry a human operator and is piloted by a remote operator using a control station. In some embodiments, the vehicle is an aquatic vehicle capable of surface or subsurface travel through and/or atop a liquid medium (e.g., water, water-ammonia solution, other water mixtures, and/or the like). Non-limiting examples of aquatic vehicles include unmanned underwater vehicles (UUVs), surface watercraft (e.g., boats, jet skis, and/or the like), amphibious watercraft, hovercraft, hydrofoil craft, and/or the like. As used herein, vehicle may refer to vehicles associated with urban air mobility (UAM).

"UAM" refers to urban air mobility, which includes all aerial vehicles and functions for aerial vehicles that are capable of performing vertical takeoff and/or vertical landing procedures. Non-limiting examples of UAM aerial vehicles include passenger transport vehicles, cargo transport vehicles, small package delivery vehicles, unmanned aerial system services, autonomous drone vehicles, and ground-piloted drone vehicles, where any such vehicle is capable of performing vertical takeoff and/or vertical landing.

"Clear air turbulence" (CAT) refers to turbulence occurring in cloudless regions. For example, CAT may include turbulence encountered outside of convective clouds. In some embodiments, CAT results from vertical currents of air in an unstable atmosphere. In some embodiments, CAT is caused by jet streams, terrain features, thunderstorm complexes, and/or the like.

"Biometric data" refers to any data representation of a biological signal, status, or condition of a living subject. For example, biometric data may include data representations of body temperature, pulse rate, respiration rate, blood pressure, heartbeat, local sweat rate, and/or the like. As another example, biometric data may include data representations of eye movement, hand movement, gait, flushing and/or the like. In still another example, biometric data may include a voice signature representative of one or more utterances of a subject. In some embodiments, biometric data includes metadata including timestamps, baselines, thresholds, deltas respective to baselines or thresholds, subject identifiers, biometric monitoring device identifiers, and/or the like.

Example Systems and Apparatuses of the Disclosure

FIG. 1 illustrates a block diagram of a networked environment that may be specially configured within which embodiments of the present disclosure may operate. Specifically, FIG. 1 depicts an example networked environment 100. As illustrated, the networked environment 100 includes one or more monitored vehicles 101, a CAT detection system 103, one or more biometric monitoring devices 104, one or more additional vehicles 105, one or more environment monitoring systems 106, and/or the like. In some embodiments, the CAT detection system 103 is configured to determine the monitored vehicle 101 has encountered a monitored vehicle event representative of CAT based at least in part on biometric data from a vehicle management system 115, one or more biometric monitoring devices 104, and/or the like. In some embodiments, the CAT detection system 103 is configured to generate, based at least in part on vehicle data, a predicted event location of the monitored vehicle event representative of CAT. In some embodiments, the CAT detection system 103 is configured to provide the predicted event location to one or more additional vehicles 105. In some embodiments, the CAT detection system 103 includes one or more ground stations configured to monitor and communicate with vehicles. For example, in an aerial context, a CAT detection system 103 may include an airline operator system or air traffic controller configured to communicate with aerial vehicles one or more air data gateways and/or the like.

In some embodiments, the CAT detection system 103 includes an apparatus 200 configured to perform various functions and actions related to enacting techniques and processes described herein for receiving and processing biometric data, vehicle data, environment data and/or the like, determining a monitored vehicle 101 has encountered a CAT, generating predicted event locations of CAT, and providing predicted event locations to additional vehicles 105. In some embodiments, the CAT detection system 103 is configured to provide data to and receive data from one or more monitored vehicles 101, one or more biometric monitoring devices 104, one or more additional vehicles 105, one or more environment monitoring systems 106, and/or the like. For example, the apparatus 200 may perform a process 500 for biometric-based CAT detection as shown in FIG. 5 and described herein. The monitored vehicle 101 may include any vehicle configured to communicate with the CAT detection system 103. The vehicle 105 may include any vehicle configured to receive communications from the CAT detection system 103. In some embodiments, a vehicle 105 may embody an additional monitored vehicle.

In some embodiments, the CAT detection system 103 includes one or more data stores 107. The various data in the data store 107 may be accessible to one or more of the apparatuses 200, the monitored vehicle 101, and/or the like. The data store 107 may be representative of a plurality of data stores 107 as can be appreciated. The data stored in the data store 107, for example, is associated with the operation of the various applications, apparatuses, and/or functional entities described herein. The data stored in the data store 107 may include, for example, subject data 109, weights 111, predicted event locations 113, and/or the like. In some embodiments, the data store 107 stores data from one or more monitored vehicles 101, biometric monitoring devices 104, vehicles 105, environment monitoring systems and/or the like. For example, the data store 107 may include biometric data 110A, 110B, vehicle data 117, weather data 121, and/or the like. Additional example aspects of the biometric data 110A, 110B, vehicle data 117, weather data 121, subject data 109, weights 111, predicted event location 113 are shown in the data architecture 300 depicted in FIG. 3 and described herein.

In some embodiments, the apparatus 200 is configured to receive biometric data 110A, 110B from one or more sensors 108A, 108B. The sensor 108A, 108B may be configured to generate one or more readings associated with a subject aboard a monitored vehicle 101. For example, the sensor 108A, 108B may generate readings indicative of subject heart rate, respiration rate, pulse, blood pressure, voice signature, eye movement frequency, blood oxygen, flushing, gait, hand movement, and/or the like. In some embodiments, a sensor 108A or sensor 108B includes a thermometer, pulse oximeter, optical sensor, camera, acoustic or other vibration or waveform sensor, pressure sensor, and/or the like.

In some embodiments, the apparatus 200 is configured to compare biometric data 110A, 110B to subject data 109 including one or more biometric abnormality thresholds. For example, the apparatus 200 may determine whether a heart rate, pulse rate, blood pressure, blood oxygen level, and/or the like meets one or more predetermined biometric abnormality thresholds. Additionally, or alternatively, in some embodiments, a vehicle management system 115 or biometric monitoring device 104 is configured to determine whether biometric data 110A, 110B meets one or more biometric thresholds 119A, 119B. In some embodiments, the apparatus 200 is configured to receive biometric data 110A, 110B and an indication that the biometric data meets one or more biometric abnormality thresholds. In some embodiments, the apparatus 200 configures one or more biometric abnormality thresholds at the vehicle management system 115, one or more biometric monitoring devices 104, and/or the like. For example, the apparatus 200 may provision a threshold 119B for blood oxygen level to the biometric monitoring device 104 to cause the biometric monitoring device 104 to store the threshold 119B and subsequently compared blood oxygen readings from a sensor 108B to the threshold 119B. As another example, the apparatus 200 may provision a first threshold 119A and a second threshold 119A for pulse rate to the vehicle management system 115, where the first threshold is associated with passengers and the second threshold is associated with crewmembers and exceeds the first threshold. The apparatus 200 may cause the vehicle management system 115 to store the first and second thresholds 119A and subsequently compare pulse rates from one or more sensors 108A, one or more biometric monitoring devices 104, and/or the like to the appropriate threshold (e.g., based on whether the pulse rate is associated with a crewmember or passenger).

In some embodiments, the apparatus 200 causes the vehicle management system 115 to automatically generate a pilot report (PIREP), eddy dissipation rate (EDR) data, and/or the like in response to biometric data 110A, 110B exceeding one or more predetermined thresholds 119A, 119B. For example, the apparatus 200 may configure a vehicle management system 115 to automatically generate and downlink a PIREP, EDR data, and/or the like in response to the vehicle management system obtaining biometric data for one or more subjects that meets a respective biometric abnormality threshold.

In various embodiments, the apparatus 200 is configured to determine whether a monitored vehicle 101 has encountered a monitored vehicle event representative of CAT based at least in part on biometric data (e.g., biometric data 110A, biometric data 110B, and/or the like). For example, the apparatus 200 is configured to determine monitored vehicle event occurrence based at least in part on whether biometric data meets one or more predetermined biometric abnormality thresholds. In some embodiments, the apparatus 200 is configured to determine whether the monitored vehicle 101 has encountered CAT further based at least in part on one or more weight values applied to one or more portions of biometric data. For example, in a scenario where a portion of biometric data is associated with a crewmember who is more accustomed to turbulence, the apparatus 200 may apply a lower weight value to the portion and/or utilize a greater biometric abnormality threshold when evaluating the portion. In another example, where a portion of biometric data is associated with a passenger who is less accustomed to turbulence, the apparatus 200 may apply a greater weight value to the portion and/or utilize a lower biometric abnormality threshold.

In some embodiments, the apparatus 200 is configured to apply weights 111 to portions of biometric data based at least in part on a classification of a subject associated with the portion. For example, biometric data may include a first portion associated with one or more passengers aboard a monitored vehicle 101 and a second portion associated with one or more crewmembers aboard the monitored vehicle 101. The crewmember may be more accustomed to turbulence and, as a result, demonstrate a lesser biological reaction to turbulence. As a result, the biometric data of the crewmember may be less predictive for determining CAT occurrence as compared to biometric data of the passenger, who may demonstrate a comparatively greater biological response to turbulence. To account for the differences in biological response level when processing the respective portions of biometric data, the apparatus 200 may apply a greater weight value to the second portion of biometric data associated with the passenger and as compared to weight value applied by the apparatus 200 to the first portion of biometric data associated with the crewmember.

In some embodiments, the apparatus 200 is configured to determine whether a monitored vehicle 101 has encountered a monitored vehicle event representative of CAT further based at least in part on vehicle data 117 from the monitored vehicle 101, weather data 121 from an environmental monitoring system 106, and/or the like. For example, the apparatus 200 may determine CAT occurrence further based at least in part on a time series record of vehicle altitude, vertical acceleration, eddy dissipation rate (EDR), one or more pilot reports (PIREPs), airspeed, vertical velocity, angle of attack, pitch rates, roll rates, vehicle location, and/or the like. In another example, the apparatus 200 may determine CAT occurrence further based at least in part on storm forecasts, jet stream intensity, and/or the like.

In some embodiments, the apparatus 200 is configured to generate a predicted event location 113 of the monitored vehicle event representing CAT. In some embodiments, the apparatus 200 generates the predicted event location based at least in part on vehicle data 117. For example, the apparatus 200 may determine a subset of vehicle data 117 that is associated with an interval in which biometric data 110A, 110B met one or more biometric abnormality threshold. The apparatus 200 may generate a predicted event location 113 based at least in part on the subset of the vehicle data 117. In some embodiments, the apparatus 200 is configured to provision one or more predicted event locations 113 to one or more vehicles 105. For example, in an aerial context, the apparatus 200 may provide a predicted event location 113 to one or more aircraft. In some embodiments, the apparatus 200 is configured to determine one or more vehicles 105 that are within a predetermined range of a predicted event location 113 or are predicted to move within the predetermined range. For example, the apparatus 200 may obtain current locations, travel pathways, and/or the like of one or more vehicles and, based thereon, determine whether a respective vehicle is within an area comprising the predicted event location (or predicted to move into the area).

In some embodiments, the apparatus 200 is configured to obtain, process, and modify travel pathways for one or more monitored vehicles 101, vehicles 105, and/or the like. For example, the apparatus 200 may obtain a travel pathway for a monitored vehicle 101 and obtain weather data 121 from an environment monitoring system 106 based at least in part on the travel pathway. In another example, the apparatus 200 may process a travel pathway to determine whether a vehicle 105 is predicted to move within an area comprising a predicted event location 113. In another example, the apparatus 200 may modify a travel pathway for one or more vehicles to circumvent an area comprising a predicted event location 113. In some embodiments, the apparatus 200 stores modified travel pathways for subsequent use in operation of one or more monitored vehicle 101. In some embodiments, the apparatus 200 provides modified travel pathways to monitored vehicles 101, vehicles 105, and/or the like, to cause the respective vehicle to circumvent an area comprising a predicted event location 113 or enable preparation of the vehicle, passengers, and crewmembers to experience CAT.

In some embodiments, the monitored vehicle 101 includes a vehicle management system 115 configured to control operation of the monitored vehicle 101. For example, the vehicle management system 115 may include one or more vehicle controls (e.g., thrust, brakes, flaps, and/or the like). In some embodiments, the vehicle management system 115 includes an autopilot and/or the like that automatically controls the monitored vehicle 101. In some embodiments, the vehicle management system 115 includes one or more sensors 108A configured to generate biometric data 110A. In some embodiments, the vehicle management system 115 is configured to receive biometric data 110B from one or more biometric monitoring devices 104. In some embodiments, the vehicle management system 115 stores one or more biometric abnormality thresholds 309A. In some embodiments, the vehicle management system 115 is configured to determine whether one or more subsets of biometric data 110A, 110B meet a respective biometric abnormality threshold 309A. In some embodiments, the vehicle management system 115 is configured to automatically carry out one or more functions in response to determining that one or more subsets of biometric data 110A, 110B meet a respective biometric abnormality threshold 309A. For example, the vehicle management system 115 may automatically generate vehicle data 117 and downlink the vehicle data and the biometric data 110A, 110B to the CAT detection system 103. In some embodiments, the vehicle management system 115 includes any number of computing device(s) and/or other system(s) embodied in hardware, software, firmware, and/or the like that obtain, process, and/or provision biometric data, vehicle data, and/or analyses thereof to a CAT detection system 103.

In some embodiments, the vehicle management system 115 is configured to generate vehicle data 117 based at least in part on readings from one or more sensors, systems, and/or the like of the monitored vehicle 101. For example, the vehicle management system 115 may generate and record vehicle locations, velocities, vertical movement speeds, pitch rates, roll rates, angles of attack, component or system statuses, and/or the like. In some embodiments, the vehicle management system 115 includes a transponder, data uplink system, traffic collision avoidance system (TCAS), automatic dependent surveillance-broadcast (ADS-B), flight recorder, and/or the like, that is configured to receive data from and provide data to a CAT detection system 103. In some embodiments, the vehicle management system 115 includes one or more displays on which vehicle data 117, biometric data 110A, 110B, weather data 121, and/or the like may be rendered. In some embodiments, the vehicle management system 115 includes one or more input devices (e.g., touchscreens, buttons, selectors, cursors, and/or the like) by which the vehicle management system receives inputs from a vehicle operator, such as a crewmember.

In some embodiments, the biometric monitoring device 104 includes any computing device configured to generate biometric data 110B for a subject. In some embodiments, the biometric monitoring device 104 includes a smartphone, smart accessory (e.g., smartwatch, and/or the like), medical device, and/or the like. The biometric monitoring device 104 may include any number of computing device(s) and/or other system(s) embodied in hardware, software, firmware, and/or the like that generate and provide biometric data 110B to a vehicle management system 115, CAT detection system 103, and/or the like. In some embodiments, the biometric monitoring device 104 includes one or more sensors 108B configured to measure one or more biological signals, conditions, statuses, and/or the like. In some embodiments, the biometric monitoring device 104 is configured to receive and store one or more biometric abnormality thresholds 309B from the CAT detection system 103, vehicle management system 115, and/or the like. In some embodiments, the biometric monitoring device 104 stores subject data 109 including subject identifiers, subject classifications, and/or the like.

In some embodiments, the biometric monitoring device 104 is configured to receive and respond to a request to provide biometric data 110B to the CAT detection system 103. In some embodiments, the biometric monitoring device 104 provides an acceptance or rejection of the request, where acceptance of the request may include historical biometric data, subject identifiers, subject classifications, and/or the like. In some embodiments, the biometric monitoring device 104 determines that one or more subsets of biometric data 110B meet one or more biometric abnormality thresholds 309B. In response to the determination, the biometric monitoring device 104 may provide the biometric data 110 (or subsets thereof) to the vehicle management system 115, CAT detection system 103, and/or the like. In some embodiments, the biometric monitoring device 104 includes one or more displays on which biometric data 110B, requests to receive biometric data, fields for responding to requests, and/or the like may be rendered. In some embodiments, the biometric monitoring device 104 includes one or more input devices (e.g., touchscreens, buttons, selectors, cursors, and/or the like) by which the biometric monitoring device receives inputs from a subject.

In some embodiments, the environment monitoring system 106 is configured to generate weather data 121 associated with one or more locations, travel pathways, and/or the like. For example, the environment monitoring system 106 may generate weather reports indicative of wind, storm, and other atmospheric conditions along a travel pathway. In some embodiments, the apparatus 200 is configured to obtain weather data from the environment monitoring system 106. In some embodiments, the environment monitoring system 106 embodies a weather station, weather service, and/or the like. For example, the environment monitoring system 106 may be a local or remote computing environment that is accessible to the CAT detection system 103, monitored vehicle 101, and/or the like.

In some embodiments, the CAT detection system 103, monitored vehicle 101, biometric monitoring device 104, vehicle 105, environment monitoring system 106, and/or the like are communicable over one or more communications network(s), for example the communications network(s) 150. It should be appreciated that the communications network 150 in some embodiments is embodied in any of a myriad of network configurations. In some embodiments, the communications network 150 embodies a public network (e.g., the Internet). In some embodiments, the communications network 150 embodies a private network (e.g., an internal, localized, and/or closed-off network between particular devices). In some other embodiments, the communications network 150 embodies a hybrid network (e.g., a network enabling internal communications between particular connected devices and external communications with other devices). In some embodiments, the communications network 150 embodies a satellite-based communication network. Additionally, or alternatively, in some embodiments, the communications network 150 embodies a radio-based communication network that enables communication between the apparatus 200 and the monitored vehicle 101. For example, the apparatus 200 may provision biometric abnormality thresholds to and receive biometric data and vehicle data from a vehicle management system 115 via a transponder, communication gateway, and/or the like. The communications network 150 in some embodiments may include one or more transponders, satellites, base station(s), relay(s), router(s), switch(es), cell tower(s), communications cable(s) and/or associated routing station(s), and/or the like. In some embodiments, the communications network 150 includes one or more user-controlled computing device(s) (e.g., a user owner router and/or modem) and/or one or more external utility devices (e.g., Internet service provider communication tower(s) and/or other device(s)).

Each of the components of the system communicatively coupled to transmit data to and/or receive data from one another over the same or different wireless or wired networks embodying the communications network 150. Such configuration(s) include, without limitation, a wired or wireless Personal Area Network (PAN), Local Area Network (LAN), Metropolitan Area Network (MAN), Wide Area Network (WAN), satellite network, radio network, and/or the like. Additionally, while FIG. 1 illustrate certain system entities as separate, standalone entities communicating over the communications network 150, the various embodiments are not limited to this particular architecture. In other embodiments, one or more computing entities share one or more components, hardware, and/or the like, or otherwise are embodied by a single computing device such that connection(s) between the computing entities are over the communications network 150 are altered and/or rendered unnecessary.

FIG. 2 illustrates a block diagram of an example apparatus 200 that may be specially configured in accordance with at least some example embodiments of the present disclosure. The apparatus 200 may carry out functionality and processes described herein to configure biometric abnormality thresholds, receive and process biometric data, generate and apply weights to biometric data, determine that a vehicle has experienced CAT based at least in part on weighted biometric data, predict locations of CAT, and/or the like. In some embodiments, the apparatus 200 includes a processor 201, memory 203, communications circuitry 205, input/output circuitry 207, and prediction circuitry 209. In some embodiments, the apparatus 200 is configured, using one or more of the processor 201, memory 203, communications circuitry 205, input/output circuitry 207, and/or prediction circuitry 209, to execute and perform the operations described herein.

In general, the terms computing entity (or "entity" in reference other than to a user), device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, controlling, modifying, restoring, processing, displaying, storing, determining, creating/generating, predicting, monitoring, evaluating, comparing, and/or similar terms used herein interchangeably. In one embodiment, these functions, operations, and/or processes may be performed on data, content, information, and/or similar terms used herein interchangeably. In this regard, the apparatus 200 embodies a particular, specially configured computing entity transformed to enable the specific operations described herein and provide the specific advantages associated therewith, as described herein.

Although components are described with respect to functional limitations, it should be understood that the particular implementations necessarily include the use of particular computing hardware. It should also be understood that in some embodiments certain of the components described herein include similar or common hardware. For example, in some embodiments two sets of circuitry both leverage use of the same processor(s), network interface(s), storage medium(s), and/or the like, to perform their associated functions, such that duplicate hardware is not required for each set of circuitry. The use of the term "circuitry" as used herein with respect to components of the apparatuses described herein should therefore be understood to include particular hardware configured to perform the functions associated with the particular circuitry as described herein.

Particularly, the term "circuitry" should be understood broadly to include hardware and, in some embodiments, software for configuring the hardware. For example, in some embodiments, "circuitry" includes processing circuitry, storage media, network interfaces, input/output devices, and/or the like. Additionally, or alternatively, in some embodiments, other elements of the apparatus 200 provide or supplement the functionality of another particular set of circuitry. For example, the processor 201 in some embodiments provides processing functionality to any of the sets of circuitry, the memory 203 provides storage functionality to any of the sets of circuitry, the communications circuitry 205 provides network interface functionality to any of the sets of circuitry, and/or the like.

In some embodiments, the processor 201 (and/or co-processor or any other processing circuitry assisting or otherwise associated with the processor) is/are in communication with the memory 203 via a bus for passing information among components of the apparatus 200. In some embodiments, for example, the memory 203 is non-transitory and may include, for example, one or more volatile and/or non-volatile memories. In other words, for example, the memory 203 in some embodiments includes or embodies an electronic storage device (e.g., a computer readable storage medium). In some embodiments, the memory 203 is configured to store information, data, content, applications, instructions, or the like, for enabling the apparatus 200 to carry out various functions in accordance with example embodiments of the present disclosure (e.g., processing biometric data, configuring biometric abnormality thresholds, determining a vehicle has encountered a monitored vehicle event representing CAT, generating a predicted event location, and/or the like). In some embodiments, the memory 203 is embodied as a data store 107 as shown in FIG. 1 and described herein. In some embodiments, the memory 203 includes subject data 109, biometric data 110, vehicle data 117, weights 111, predicted event locations 113, and/or the like, as further architected in FIG. 3 and described herein.

The processor 201 may be embodied in a number of different ways. For example, in some embodiments, the processor 201 includes one or more processing devices configured to perform independently. Additionally, or alternatively, in some embodiments, the processor 201 includes one or more processor(s) configured in tandem via a bus to enable independent execution of instructions, pipelining, and/or multithreading. The use of the terms "processor" and "processing circuitry" should be understood to include a single core processor, a multi-core processor, multiple processors internal to the apparatus 200, and/or one or more remote or "cloud" processor(s) external to the apparatus 200.

In an example embodiment, the processor 201 is configured to execute instructions stored in the memory 203 or otherwise accessible to the processor. Additionally, or alternatively, the processor 201 in some embodiments is configured to execute hard-coded functionality. As such, whether configured by hardware or software methods, or by a combination thereof, the processor 201 represents an entity (e.g., physically embodied in circuitry) capable of performing operations according to an embodiment of the present disclosure while configured accordingly. Additionally, or alternatively, as another example in some example embodiments, when the processor 201 is embodied as an executor of software instructions, the instructions specifically configure the processor 201 to perform the algorithms embodied in the specific operations described herein when such instructions are executed.

As one particular example embodiment, the processor 201 is configured to perform various operations associated with determining a vehicle has encountered a monitored vehicle event representing CAT and generating a predicted event location for the monitored vehicle event. In some embodiments, the processor 201 includes hardware, software, firmware, and/or the like, that generate biometric abnormality thresholds, process biometric data, vehicle data, weather data, and/or the like, initiate functionality at one or more biometric monitoring devices 104, vehicle management systems 115, and/or the like, modify travel pathways, determine subject classifications, and/or the like. For example, the processor 201 may generate and configure one or more biometric abnormality thresholds at one or more biometric monitoring devices 104, vehicle management systems 115, and/or the like. As another example, the processor 201 may determine a subset of vehicle data, weather data, and/or the like that is associated with an interval in which a vehicle is determined to have encountered a monitored vehicle event representing CAT. As another example, the processor 201 may instruct a vehicle management system 115 to automatically generate and provide vehicle data in response to obtaining biometric data that meets one or more biometric abnormality thresholds. In still another example, the processor 201 may obtain and store subject data indicative of a subject classification and approval to obtain biometric data from a biometric monitoring device 104.

In some embodiments, the apparatus 200 includes input/output circuitry 207 that provides output to a user (e.g., an operating entity of a CAT detection system 103, monitored vehicle 101, vehicle 105, and/or the like) and, in some embodiments, receives an indication of a user input. For example, in some contexts, the input/output circuitry 207 provides output to and receives input from one or more system operators, vehicle crewmembers, biometric monitoring device users, and/or the like. In some embodiments, the input/output circuitry 207 is in communication with the processor 201 to provide such functionality. The input/output circuitry 207 may comprise one or more user interface(s) and in some embodiments includes a display that comprises the interface(s) rendered as a web user interface, an application user interface, a user device, a backend system, or the like. In some embodiments, the input/output circuitry 207 also includes a keyboard, a mouse, a joystick, a touch screen, touch areas, soft keys a microphone, a speaker, and/or other input/output mechanisms. The processor 201 and/or input/output circuitry 207 comprising the processor may be configured to control one or more functions of one or more user interface elements through computer program instructions (e.g., software and/or firmware) stored on a memory accessible to the processor 201 (e.g., memory 203, and/or the like). In some embodiments, the input/output circuitry 207 includes or utilizes a user-facing application to provide input/output functionality to a display of a CAT detection system 103, monitored vehicle 101, biometric monitoring device 104, vehicle 105, environment monitoring system 106, and/or other display associated with a user.

In some embodiments, the apparatus 200 includes communications circuitry 205. The communications circuitry 205 includes any means such as a device or circuitry embodied in either hardware or a combination of hardware and software that is configured to receive and/or transmit data from/to a network and/or any other device, circuitry, or module in communication with the apparatus 200. In this regard, in some embodiments the communications circuitry 205 includes, for example, a network interface for enabling communications with a wired or wireless communications network, such as the network 150 shown in FIG. 1 and described herein. Additionally, or alternatively in some embodiments, the communications circuitry 205 includes one or more network interface card(s), antenna(s), bus(es), switch(es), router(s), modem(s), and supporting hardware, firmware, and/or software, or any other device suitable for enabling communications via one or more communications network(s). Additionally, or alternatively, the communications circuitry 205 includes circuitry for interacting with the antenna(s) and/or other hardware or software to cause transmission of signals via the antenna(s) or to handle receipt of signals received via the antenna(s). In some embodiments, the communications circuitry 205 enables transmission to and/or receipt of data from a vehicle management system 115, biometric monitoring device 104, vehicle 105, environment monitoring system 106 and/or other external computing devices in communication with the apparatus 200.

The prediction circuitry 209 includes hardware, software, firmware, and/or a combination thereof, that carry out various functionality described herein to determine that a vehicle has encountered a monitored vehicle event representing CAT and generate a predicted location of the CAT. For example, in some contexts, the prediction circuitry 209 includes hardware, software, firmware, and/or the like, that process biometric data, vehicle data, weather data, and/or the like based at least in part on one or more biometric abnormality thresholds, weights, subject classifications, and/or the like to determine whether a vehicle has encountered a monitored vehicle event representing CAT. In some embodiments, the prediction circuitry 209 includes hardware, software, firmware, and/or the like, that generate a predicted location of CAT based at least in part on a subset of vehicle data associated with time interval during which biometric data for one or more subjects aboard a monitored vehicle met one or more biometric abnormality thresholds. In some embodiments, the prediction circuitry 209 includes hardware, software, firmware, and/or the like, that apply weights to subsets of biometric data based respective associations of the subsets with one or more subject classifications. For example, the prediction circuitry 209 may apply a first weight to a subset of biometric data associated with a crewmember classification and a second weight to a subset of biometric data associated with a passenger classification, where the second weight is associated with a greater impact value as compared to the first weight. In doing so, the prediction circuitry 209 may assign a greater impact to the passenger-associated biometric data when determining whether a vehicle has encountered a monitored vehicle event representing CAT and generating a predicted location of the monitored vehicle event.

In some embodiments, the prediction circuitry 209 includes hardware, software, firmware, and/or the like, that compensate vehicle data, weather data, and/or the like based at least in part on biometric data or associated metadata. For example, the prediction circuitry 209 may process biometric data and metadata to determine a time interval within which one or more subsets of the biometric data met a biometric abnormality threshold. The prediction circuitry 209 may compensate EDR data, weather reports, vehicle location data, and/or the like based at least in part on the time interval to obtain data that corresponds to operation of the vehicle during a monitored vehicle event representing CAT. In some embodiments, the prediction circuitry 209 includes a separate processor, specially configured field programmable gate array (FPGA), and/or a specially programmed application specific integrated circuit (ASIC).

Additionally, or alternatively, in some embodiments, two or more of the processor 201, memory 203, communications circuitry 205, input/output circuitry 207, and/or prediction circuitry 209 are combinable. Additionally, or alternatively, in some embodiments, one or more of the sets of circuitry perform some or all of the functionality described associated with another component. For example, in some embodiments, two or more of the sets of circuitry 201-209 are combined into a single module embodied in hardware, software, firmware, and/or a combination thereof. Similarly, in some embodiments, one or more of the sets of circuitry, for example the memory 203, communication interface 205, and/or prediction circuitry 209 is/are combined with the processor 201, such that the processor 201 performs one or more of the operations described above with respect to each of these sets of circuitry 203-209.

Example Data Architecture of the Disclosure

Having described example systems and apparatuses in accordance with embodiments of the present disclosure, example architectures of data in accordance with the present disclosure will now be discussed. In some embodiments, the systems and/or apparatuses described herein maintain data environment(s) that enable the workflows in accordance with the data architectures described herein. For example, in some embodiments, the systems and/or apparatuses described herein function in accordance with the data architectures depicted and described herein with respect to FIG. 3 are maintained via the apparatus 200.

FIG. 3. illustrates an example data architecture 300 in accordance with at least some example embodiments of the present disclosure. In some embodiments, the biometric data 110 includes any data representation of a biological signal, status, or condition of a living subject. In some embodiments, the biometric data 110 includes blood oxygen level 301, heart rate 303, blood pressure 305, and/or the like. As another example, the biometric data 110 may include eye movement frequency, facial geometry, and/or the like. In some embodiments, the biometric data includes metadata 307. In some embodiments, the metadata 307 includes one or more timestamps associated with generation or measurement of biometric signals, statuses, conditions, and/or the like. In some embodiments, the metadata 307 includes a subject identifier, subject classification, and/or the like. In some embodiments, the metadata 307 includes one or more biometric baselines, biometric abnormality thresholds, delta values respective to baselines or thresholds, and/or the like.

In some embodiments, the subject data 109 includes one or more biometric abnormality thresholds 309. For example, the subject data 109 may include a first biometric abnormality threshold for heart rate and a second biometric abnormality threshold for blood oxygen level. In some embodiments, the biometric abnormality threshold 309 is associated with one or more subject identifiers 311, one or more subject classifications 313, and/or the like. For example, a biometric abnormality threshold 309 may be associated with a subject identifier 311 for a particular passenger, crewmember, and/or the like. Additionally, or alternatively, the biometric abnormality threshold 309 may be associated with a passenger classification, a crewmember classification, and/or the like. In some embodiments, the biometric abnormality threshold 309 is generated based at least in part on historical biometric data 315.

In some embodiments, the subject data 109 includes one or more subject identifiers 311. In some embodiments, the subject identifier 311 uniquely identifies a biometric monitoring device 104, a subject carrying a biometric monitoring device 104, a subject aboard a monitored vehicle 101, and/or the like. In some embodiments, the subject identifier 311 includes a numeric or alphanumeric string. In one example, the subject identifier 311 may be a device identifier, such as a media access control (MAC) address, internet protocol (IP) address, international mobile equipment identity (IMEI) number, serial number, model number, and/or the like. In some embodiments, the subject data 109 includes one or more subject classifications 313 that associate a subject identifier 311 (and, as a result, a subject, biometric monitoring device, and/or the like) with one or more classifications. In some embodiments a subject classification 313 includes a passenger classification, crewmember classification, and/or the like. In some embodiments, the subject classification 313 includes one or more age ranges. For example, the subject classification 313 may include age ranges of 0-3, 4-9, 10-13, 13-18, 21+, and/or the like. In another example subject classification 313 may include age classifications, such as infant, toddler, young child, teen, adult, senior, and/or the like. In some embodiments, the subject classification 313 includes experience levels of subjects aboard a vehicle. For example, in an aerial context, the subject classification 313 may include first time flyer, occasional flyer, frequent flyer, daily flyer, and/or the like.

In some embodiments, the subject data 109 includes historical biometric data 315. In some embodiments, the historical biometric data 315 includes historical blood oxygen levels, heart rates, blood pressures, eye movement frequencies, and/or the like. In some embodiments, one or more subsets of the historical biometric data 315 are associated with biological responses of one or more subjects under nominal conditions (e.g., resting, non-duress, and/or the like). For example, one or more subsets of the historical biometric data 315 are associated with biological responses of one or more subjects aboard a monitored vehicle that is not experiencing a monitored vehicle event representative of CAT. In some embodiments, one or more subsets of the historical biometric data 315 are associated with biological responses of one or more subjects under turbulent conditions. For example, one or more subsets of the historical biometric data 315 are associated with recorded biological responses of subjects aboard a monitored vehicle during a monitored vehicle event representing CAT.

In some embodiments, historical biometric data is used to generate one or more biometric abnormality thresholds 309. In some embodiments, biometric data 110 is compared to one or more biometric abnormality thresholds 309 to determine whether one or more thresholds are met, which may be indicative of a vehicle encountering a monitored vehicle event representing CAT. In some embodiments, one or more weights 111 are applied to one or more subsets of biometric data 110 to influence an impact value of the subset of biometric data 110 on determinations of whether the monitored vehicle 101 has encountered a monitored vehicle event representing CAT. In some embodiments, the weights 111 include different weight values associated with different subject classifications, subject identifiers, and/or the like. In some embodiments, the weights 111 include a first weight 317 that is associated with a crewmember classification and a second weight 319 that is associated with a passenger classification. In some embodiments, the second weight 319 is associated with a greater impact value as compared to the first weight 317 such that processes for detecting CAT attribute greater predictiveness to biometric data associated with passengers as compared to biometric data associated with crewmembers.

In some embodiments, the vehicle data 117 includes any data associated with operations, conditions, or statuses of a monitored vehicle 101 or vehicle 105. In some embodiments, the vehicle data 117 includes one or more locations 310. For example, the vehicle data 117 may include a current location, one or more historical locations, and/or the like of a monitored vehicle 101. In some embodiments, the vehicle data 117 includes a travel pathway for a vehicle. For example, in an aerial context, the vehicle data 117 may include a flight path for a monitored vehicle 101. In some embodiments, the vehicle data 117 includes one or more vehicle identifiers that uniquely identify a vehicle. For example, the vehicle data 117 may include a model number, serial number, registration, and/or the like of a monitored vehicle. In some embodiments, the vehicle data 117 includes eddy dissipation rate (EDR) data 312. In some embodiments the EDR data 312 includes one or more vehicle speeds, angles of attack, pitch rates, roll rates, angles, vertical speeds, altitudes, and/or the like.

In some embodiments, the vehicle data 117 includes one or more pilot reports (PIREPs) 314. In some embodiments, the PIREP 314 includes conditions encountered by a vehicle during navigation along a travel pathway. For example, the PIREP 314 may include descriptions of weather, turbulence, traffic, and/or the like encountered by a monitored vehicle 101. In some embodiments the PIREP 314 includes one or more turbulence frequencies. For example, the PIREP 314 may indicate intermittent, occasional, or continuous turbulence along one or more portions of a travel pathway. In some embodiments, the PIREP 314 includes one or more turbulence intensities. For example, the PIREP 314 may indicate light, moderate, severe, or extreme turbulence along one or more portions of a travel pathway. In some embodiments, one or more subset of vehicle data 117 are used to further determine that a monitored vehicle 101 has encountered a monitored vehicle event representing CAT. For example, a method of the present disclosure may include determining that a monitored vehicle 101 has encountered a monitored vehicle event representing CAT based on biometric data 110 and further based at least in part on a pilot report (PIREP) associated with the monitored vehicle.

In some embodiments, a monitored vehicle 101 is determined to have encountered a monitored vehicle event representing CAT based at least in part on one or more subsets of biometric data 110, one or weights 111 applied to respective subsets of biometric data 110, one or biometric abnormality thresholds, and/or the like. In response to the determination, a predicted event location 113 may be generated based at least in part on vehicle data 117. In some embodiments, the predicted event location 113 is generated based at least in part on a subset of vehicle data 117 that is associated with an interval during which one or more subsets of biometric data 110 met a respective biometric abnormality threshold 309. In some embodiments, the predicted event location 113 includes one or more geographic coordinates, elevations, altitudes, timestamps, and/or the like at which the monitored vehicle event is predicted to have occurred.

In some embodiments, the weather data 121 includes data associated with one or more jet streams or other wind conditions. For example, the weather data 121 may include one or more wind directions, frequencies, velocities, and/or the like. In some embodiments, the weather data 121 includes one or more storm conditions, locations, and/or the like. In some embodiments, the weather data 121 includes one or more atmospheric conditions including temperatures, pressures, humidities, and/or the like. In some embodiments, one or more subset of weather data 121 are used to further determine that a monitored vehicle 101 has encountered a monitored vehicle event representing CAT. For example, a method of the present disclosure may include determining that a monitored vehicle 101 has encountered a monitored vehicle event representing CAT based on biometric data 110 and further based at least in part on weather data 121 associated with a travel pathway of the monitored vehicle.

Example Existing Approach

FIG. 4 shows an example existing approach to CAT detection in an aerial context. When aerial vehicles are in route to a destination, there exists a possibility of encountering clear air turbulence (CAT). In existing approaches, CAT may be impossible to detect with onboard instruments or the naked eye of a vehicle operator, thereby limiting the ability to predict and avoid CAT. During the cruise stages of flight, CAT can cause an aerial vehicle to buffet hundreds of feet with potential to damage the occupants of the aerial vehicle (e.g., passengers, crewmembers, cargo, and/or the like). Further, CAT intensity and frequency is predicted to increase due to stronger jet streams, increasing wind speeds, and stronger north-south temperature changes. In existing approaches, CAT detection relies upon weather forecast reports with delayed update rates (e.g., 6 hours or greater latency) and downlinks of eddy dissipation rate (EDR) data and manually generated pilot reports (PIREPs). The generation and downlink of EDR data and PIREPs must be manually initiated by the vehicle operator. Thus, existing approaches to detecting and reporting CAT are reliant upon manual processes and subjective opinions of a vehicle operator. As a result, the latencies and subjectivities of generating and downlinking EDR data and PIREP may result in CAT detection failure and/or inaccurate estimation of CAT location.

For example, as shown in FIG. 4, an aerial vehicle 401 may experience a CAT event 403 at a first time interval 404. In existing approaches, the determination that the aerial vehicle 401 has experienced the CAT event 403 may be based upon subjective opinion of the vehicle operator. Further, the generation and downlink of EDR data and a PIREP defining the CAT event 403 is manually initiated by the vehicle operator. The latency and subjectivity of the vehicle operator's actions may result in delays between the encountering of the CAT event 403 and initiation of an EDR measurement 405. For example, the CAT event 403 may occur at the first time interval 404 and the EDR measurement 405 may occur at a second time interval 406, where the second time interval 406 may occur minutes after the first time interval 404. Further, the performance of the EDR measurement 405 may require additional seconds or minutes. Due to the delta in vehicle position between encountering the CAT event 403, determining the CAT event occurred, and obtaining EDR data generation, the prediction of where and when the CAT was encountered may be inaccurate. The aerial vehicle 401 may travel tens of miles and ascend or descend thousands of feet or greater between the first time interval 404 and the second time interval 406. For example, one minute of latency in an operating determining the aerial vehicle 401 has encountered CAT and initiating EDR measurement 405 may result in at least 7-10 miles of deviation when generating the position of the aircraft.

In various embodiments, the method, apparatus, and computer program product described herein and shown in FIGS. 1-3, and 5 overcome these technical challenges based at least in part by utilizing biometric data to detect monitored vehicle events representative of CAT and automatically initiate prediction of the event location. For example, embodiments of the present disclosure introduce a method, apparatus, and computer program product to compensate latencies in CAT detection and event prediction based on biometric data of one or more subjects aboard a vehicle. In some embodiments, the method includes obtaining real-time biometric data associated with one or more subjects aboard a vehicle, where one or more subsets of the biometric data meet one or more biometric abnormality thresholds. In some embodiments, the method causes a vehicle management system to automatically generate and provide vehicle data corresponding to an interval in which the biometric data met one or more biometric abnormality thresholds. In doing so, the location of the vehicle during the CAT event may be more accurately and rapidly generated, thereby improving the accuracy of predicting CAT location.

In some embodiments, the method includes applying one or more weights to one or more subsets of the biometric data and/or utilizing a particular biometric abnormality threshold based on whether the subset is associated with a passenger or crewmember. In doing so, biometric data that is most predictive for detecting CAT, such as passenger biometric data, may be assigned greater impact value when determining whether the vehicle has encountered a monitored vehicle event representing CAT. In some embodiments, the method includes determining the vehicle has encountered a monitored vehicle event based at least in part on a first weighted subset of the biometric data associated with one or more passengers and a second weighted subset of the biometric associated with one or more crewmembers. In some embodiments, the method includes generating a predicted event location based at least in part on vehicle data associated with the interval at or during which one or more subsets of the biometric data met a respective biometric abnormality threshold. In some embodiments, the method includes providing the predicted event location to one or more vehicles, ground stations, and/or the like. In doing so, the method may improve awareness, mitigation, and/or avoidance of CAT.

Example Processes of the Disclosure

Having described example systems and apparatuses, data architectures, and data flows in accordance with the disclosure, example processes of the disclosure will now be discussed. It will be appreciated that each of the flowcharts depicts an example computer-implemented process that is performable by one or more of the apparatuses, systems, devices, and/or computer program products described herein, for example utilizing one or more of the specially configured components thereof.

The blocks indicate operations of each process. Such operations may be performed in any of a number of ways, including, without limitation, in the order and manner as depicted and described herein. In some embodiments, one or more blocks of any of the processes described herein occur in-between one or more blocks of another process, before one or more blocks of another process, in parallel with one or more blocks of another process, and/or as a sub-process of a second process. Additionally, or alternatively, any of the processes in various embodiments include some or all operational steps described and/or depicted, including one or more optional blocks in some embodiments. With regard to the flowcharts illustrated herein, one or more of the depicted block(s) in some embodiments is/are optional in some, or all, embodiments of the disclosure. Optional blocks are depicted with broken (or "dashed") lines. Similarly, it should be appreciated that one or more of the operations of each flowchart may be combinable, replaceable, and/or otherwise altered as described herein.

FIG. 5 illustrates a flowchart depicting operations of an example process 500 for detecting a monitored vehicle event representative of CAT in accordance with at least some example embodiments of the present disclosure. In some embodiments, the process 500 is embodied by computer program code stored on a non-transitory computer-readable storage medium of a computer program product configured for execution to perform the process as depicted and described. Additionally, or alternatively, in some embodiments, the process 500 is performed by one or more specially configured computing devices, such as apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 203 and/or another component depicted and/or described herein and/or otherwise accessible to the apparatus 200, for performing the operations as depicted and described.

In some embodiments, the apparatus 200 is in communication with one or more internal or external apparatus(es), system(s), device(s), and/or the like, to perform one or more of the operations as depicted and described. For example, the apparatus 200 may communicate with one or more sensors, one or more biometric monitoring devices 104, one or more vehicle management systems 115 of a monitored vehicle 101, one or more vehicles 105, one or more environment monitoring systems 106, and/or the like to perform one or more operations of the process 500.

At operation 503, the apparatus 200 optionally includes means such as the prediction circuitry 209, the communications circuitry 205, the input/output circuitry 207, the processor 201, and/or the like, or a combination thereof, that receive approval to obtain biometric data from one or more biometric monitoring devices. For example, the apparatus 200 may cause provision of a request to a biometric monitoring device 104. The request may embody a request to receive real-time biometric data 110 from the biometric monitoring device 104. The apparatus 200 may receive a response to the request, where the response indicates approval or rejection of the request for biometric data. In some embodiments, in response to receiving approval of the request, the apparatus 200 causes the biometric monitoring device 104 to provide biometric data to the apparatus in real-time or at a predetermined frequency (e.g., every 30 seconds, 60 seconds, or other suitable value). Additionally, or alternatively, the apparatus 200 pulls biometric data from the biometric monitoring device in real-time or at a predetermined frequency.

In some embodiments, the apparatus 200 causes provision of the request in response to the biometric monitoring device 104 moving within a predetermined proximity of a monitored vehicle 101. In some embodiments, the apparatus 200 causes provision of the request in response to a biometric monitoring device 104 connecting to one or more networks 150. For example, a passenger or crewmember may board a monitored vehicle 101 and connect their biometric monitoring device 104 to an onboard wireless fidelity (WiFi) network. As a step of connecting the biometric monitoring device 104, the apparatus 200 may cause rendering of the request for biometric data on a display of the biometric monitoring device.

In various embodiments, in response to receiving approval of the request, the apparatus 200 obtains historical biometric data associated with the subject carrying the biometric monitoring device 104. For example, the apparatus 200 may receive the historical biometric data from the biometric monitoring device 104. As another example, the apparatus 200 may receive the historical biometric data from a remote computing environment associated with the biometric monitoring device 104. The apparatus 200 may receive an approval of the request including a token, identifier, key, and/or the like, which the apparatus 200 may provide to a remote computing environment to obtain historical biometric data associated with the biometric monitoring device 104 or subject.

In some embodiments, in response to receiving approval of the request, the apparatus 200 stores subject data associated with the biometric monitoring device or subject. For example, the apparatus 200 may obtain and store a subject identifier, subject classification, historical biometric data, and/or the like. In some embodiments, the apparatus 200 provides a second request to the biometric monitoring device 104 that requests a classification of the subject as either a crewmember of the monitored vehicle 101 or passenger. For example, the apparatus 200 may cause rendering of a GUI on a display of the biometric monitoring device, where the GUI includes selectable fields for passenger and crewmember classifications. The apparatus 200 may receive the classification of the subject and store a subject classification (e.g., passenger or crewmember) in association with an identifier for the biometric monitoring device 104. In some embodiments, the apparatus 200 receives a classification of one or more subjects aboard the monitored vehicle 101 from a vehicle management system 115. For example, the apparatus 200 may receive a respective classification of one or more subjects aboard the monitored vehicle 101 as either passenger or crewmember such that biometric data received in association with the subject may be associated with the subject classification.

At operation 506, the apparatus 200 optionally includes means such as the prediction circuitry 209, the communications circuitry 205, the input/output circuitry 207, the processor 201, and/or the like, or a combination thereof, that generate one or more biometric abnormality thresholds. For example, the apparatus 200 may generate one or more biometric abnormality thresholds based at least in part on historical biometric data associated with one or more subjects. In some embodiments, the apparatus 200 generates a respective biometric abnormality threshold for a plurality of biometric signals. For example, the apparatus 200 may generate a first biometric abnormality threshold for blood oxygen level, a second biometric abnormality threshold for blood pressure, and a third biometric abnormality threshold for heart rate. In some embodiments, the biometric abnormality threshold defines a data value or range at, above, or beneath which the corresponding biometric signal is determined to meet the threshold.

In some embodiments, the apparatus 200 generates one or more biometric baselines based at least in part on historical biometric data, one or more stored rules or policies, and/or the like. For example, the apparatus 200 may generate a blood pressure baseline for one or more subjects based at least in part on respective historical blood pressures for the one or more subjects. In some embodiments, the apparatus 200 generates a biometric abnormality threshold based at least in part on the biometric baseline. For example, the biometric abnormality threshold may be generated based at least in part on a predefined delta applied to the biometric baseline. In some embodiments, the biometric abnormality threshold includes one or more relationships or associative rules between multiple types of biometric data. For example, a biometric abnormality threshold may include a first threshold value for pulse rate and a second threshold value for respiration rate such that satisfaction of the biometric abnormality threshold requires one or more both points of biometric data to meet the corresponding threshold. In some embodiments, the apparatus 200 obtains a respective biometric abnormality threshold for a plurality of subjects aboard the monitored vehicle 101.

Alternatively, or additionally, in some embodiments, the apparatus 200 obtains a respective biometric abnormality threshold for a first subset of subjects associated with a passenger classification and a second subset of subjects associated with a crewmember classification, where the biometric abnormality threshold for the crewmember classification may be greater than the biometric abnormality threshold for the passenger classification. In some embodiments, the apparatus 200 receives a respective biometric abnormality threshold, biometric baseline, and/or the like from a biometric monitoring device 104, vehicle management system 115, and/or the like. In some embodiments, a biometric abnormality threshold includes a threshold number of subjects such that satisfaction of the biometric abnormality threshold may require the threshold number of subjects or biometric monitoring devices demonstrating biometric data that meets one or more values specified by the biometric abnormality threshold. In various embodiments, the apparatus 200 stores the biometric abnormality threshold as subject data in association with a subject identifier, subject classification, and/or the like.

At operation 509, the apparatus 200 optionally includes means such as the prediction circuitry 209, the communications circuitry 205, the input/output circuitry 207, the processor 201, and/or the like, or a combination thereof, that configure one or more biometric abnormality thresholds at one or more biometric monitoring devices, a vehicle management system of the monitored vehicle, and/or the like. For example, the apparatus 200 may configure a respective biometric abnormality threshold at a plurality of biometric monitoring devices 104 carried by subjects aboard the monitored vehicle 101. As another example, the apparatus 200 may configure one or more biometric abnormality thresholds at a vehicle management system 115 of the monitored vehicle 101. In some embodiments, configuring a biometric abnormality threshold includes the apparatus 200 causing provision of the biometric abnormality threshold to one or more biometric monitoring devices, vehicle management systems, and/or the like to cause the biometric monitoring device, vehicle management system, and/or the like to store the biometric abnormality threshold.

In some embodiments, the apparatus 200 commands the biometric monitoring device, vehicle management system, and/or the like to compare biometric data to the biometric abnormality threshold in real-time to perform one or more actions in response to determining that biometric data meets the biometric abnormality threshold. For example, apparatus 200 may command the vehicle management system 115 to generate and/or compensate an eddy dissipation rate (EDR) based on a time interval in which biometric data for one or more passengers, crewmembers, and/or the like met a respective biometric abnormality threshold. As another example, the apparatus 200 may command the vehicle management system 115 to generate and provide to the apparatus a pilot report, vehicle data, and/or the like in response to the biometric data meeting a respective biometric abnormality threshold. In another example, the apparatus 200 commands the vehicle management system 115, one or more biometric monitoring devices 104, and/or the like to provide an indication to the apparatus in response to biometric data meeting one or more biometric abnormality thresholds. Additionally, or alternatively, the apparatus 200 instructs the vehicle management system 115, one or more biometric monitoring devices 104, and/or the like to provide biometric data to the apparatus in response to at least a subset of the biometric data meeting one or more biometric abnormality thresholds.

At operation 512, the apparatus 200 includes means such as the prediction circuitry 209, the communications circuitry 205, the input/output circuitry 207, the processor 201, and/or the like, or a combination thereof, that receive biometric data that meets one or more biometric abnormality thresholds. For example, the apparatus 200 may receive biometric data from a vehicle management system 115, one or more biometric monitoring devices 104, and/or the like, where one or more subsets of the biometric data meet one or more biometric abnormality thresholds. Alternatively, in some embodiments, the apparatus 200 receives from the vehicle management system 115, one or more biometric monitoring devices 104, and/or the like an indication that one or more subsets of biometric data meet a respective biometric abnormality threshold. In such embodiments, in response to receiving the indication, the apparatus 200 may obtain the biometric data from the vehicle management system 115 and/or biometric monitoring device 104. Additionally, or alternatively, the apparatus 200 may obtain the biometric data from a remote computing environment configured to receive and store biometric data from the vehicle management system or biometric monitoring device.

In some embodiments, the biometric data includes measurements of biometric signals for one or more subjects aboard the monitored vehicle 101. In some embodiments, the biometric data includes heart rate, respiration rate, pulse rate, blood pressure, voice signature, eye movement frequency, blood oxygen level, facial recordings, and/or the like. The biometric data received may include biometric data that meets one or more biometric abnormality thresholds. In some embodiments, the biometric data received includes biometric data that is associated with the same time interval as the threshold-satisfying biometric data but does not itself satisfy a biometric abnormality threshold. In some embodiments, the received biometric data includes biometric data associated with a predetermined time interval comprising a timestamp in which one or more subsets of biometric data met a respective biometric abnormality threshold. The predetermined time interval may comprise an interval preceding the timestamp, an interval containing the timestamp, an interval following the timestamp, and/or the like. For example, the apparatus 200 may receive a subset of biometric data associated with a timestamp at which one or more biometric abnormality thresholds were met, a second subset of biometric data for an interval preceding the timestamp (e.g., 30 seconds, 1 minute, 5 minutes, or another suitable value), and a third subset of biometric data associated with an interval following the timestamp (e.g., 30 seconds, 1 minute, 5 minutes, or another suitable value). In some embodiments, the received biometric data includes or indicates the biometric abnormality threshold that was met. In some embodiments, the received biometric data includes a respective delta for one or more subsets of the biometric data respective to one or more biometric abnormality thresholds.

In some embodiments, the received biometric data includes metadata including one or more timestamps, one or more subject classifications (e.g., passenger, crewmember, and/or the like), one or more subject identifiers, and/or the like. For example, the biometric data received by the apparatus may include a first subset associated with one or more passengers and a second subset associated with one or more crewmembers. The biometric data may include a corresponding subject classification for the first and second subsets. Alternatively, in some embodiments, the apparatus 200 determines the subject classification of one or more subsets of the biometric data based at least in part on one or more subject identifiers. For example, the apparatus 200 may obtain a subject identifier associated with a subset of biometric data, such as a device identifier for a biometric monitoring device 104 that generated the biometric data. The apparatus 200 may determine a subject classification for the subject carrying the biometric monitoring device 104 based at least in part on the subject identifier.

In some embodiments, the apparatus 200 determines a respective subject classification for one or more subsets of the biometric data based on metadata from the vehicle management system 115. For example, the metadata may include a location within the monitored vehicle 101 where the subset of the biometric data was obtained. In response to the location embodying a cockpit, galley, command center, and/or the like of the monitored vehicle 101, the apparatus 200 may determine that the subset is associated with a crewmember subject classification. In response to the location embodying a cabin region of the monitored vehicle 101, the apparatus 200 may determine that the subset is associated with a passenger subject classification.

At operation 518, the apparatus 200 optionally includes means such as the prediction circuitry 209, the communications circuitry 205, the input/output circuitry 207, the processor 201, and/or the like, or a combination thereof, that receive vehicle data associated with the monitored vehicle 101. For example, the apparatus 200 may receive vehicle data from the vehicle management system 115. In some embodiments, the apparatus 200 (or the vehicle management system 115) compensates the vehicle data based at least in part on a timestamp associated with the one or more portions of biometric data that met a respective biometric abnormality threshold. For example, the apparatus 200 may partition the vehicle data based at least in part on the timestamp to obtain a subset of vehicle data associated with an interval comprising the timestamp. The subset of vehicle data may correspond to an interval during which the monitored vehicle 101 encountered a monitored vehicle event representing CAT. In some embodiments, the vehicle data includes vehicle location (e.g., geographical coordinates, elevation, heading, bearing, and/or the like), vehicle speed (e.g., airspeed, ground speed, ascent speed, descent speed, and/or the like), vehicle pitch, vehicle altitude, and/or the like. In some embodiments, the vehicle data includes one or more eddy dissipation rates (EDRs) associated with an interval comprising, preceding, or proceeding the timestamp at which a respective biometric abnormality threshold was met. In some embodiments, the vehicle data includes one or more PIREPs, where a respective PIREP is automatically generated in response to one or more biometric abnormality thresholds being met.

At operation 518, the apparatus 200 optionally includes means such as the prediction circuitry 209, the communications circuitry 205, the input/output circuitry 207, the processor 201, and/or the like, or a combination thereof, that receive weather data. For example, the apparatus 200 may receive weather data from an environment monitoring system 106, such as a weather forecasting service. In some embodiments, the weather data includes one or more wind speeds, wind directions, temperatures, pressures, humidities, storm forecasts, and/or the like. In some embodiments, the weather data is associated with one or more physical regions that comprise a current or historical location of the monitored vehicle 101. In some embodiments, the apparatus 200 compensates one or more sets of weather data based at least in part on a timestamp associated with the one or more portions of biometric data that met a respective biometric abnormality threshold.

At operation 521, the apparatus 200 includes means such as the prediction circuitry 209, the communications circuitry 205, the input/output circuitry 207, the processor 201, and/or the like, or a combination thereof, that apply weight values to portions of the biometric data. A respective weight value may be associated with a subject classification, such as passenger or crewmember. For example, the apparatus 200 may apply a first weight 111 to one or more subsets of the biometric data that are associated with a crewmember classification and a second weight 111 to one or more subsets of the biometric data that are associated with a passenger classification. The second weight 111 may comprise a greater impact value as compared to the first weight value 111. For example, passengers may demonstrate a greater biological response to CAT as compared to crewmembers that experience CAT on a more frequent basis. The apparatus 200 may apply a greater weight value to biometric data associated with a passenger (as compared to biometric data associated with a crewmember) to account for the increased predictiveness of the passenger's biological response in detecting CAT. In some embodiments, the apparatus 200 filters the received biometric data to generate a first subset comprising biometric data tagged as passenger data and a second subset comprising biometric data tagged as crewmember data.

In some embodiments, where subsets of biometric data are associated with different passengers, different crewmembers, and/or the like, the apparatus 200 applies a subject-specific weight 111 to the respective subset of biometric data. The apparatus 200 may generate the subject-specific weight value based at least in part on a subject classification of the subject, historical biometric data associated with the subject, historical vehicle data associated with the historical biometric data, and/or the like. In some embodiments, based on the combination of a subject's historical biometric data and historical vehicle data, the apparatus 200 determines the subject's biological response under turbulent and non-turbulent vehicle conditions such that the apparatus may compare the received biometric data to the historical biometric data and/or historical vehicle data to generate the weight 111.

At operation 524, the apparatus 200 includes means such as the prediction circuitry 209, the communications circuitry 205, the input/output circuitry 207, the processor 201, and/or the like, or a combination thereof, that determine the monitored vehicle has encountered a monitored vehicle event representing CAT. For example, the apparatus 200 may determine that the monitored vehicle 101 has encountered a monitored vehicle event representing CAT based at least in part on one or more subsets of the biometric data and one or more weights applied to a respective subset of the biometric data. Alternatively, in some embodiments, the apparatus 200 configures the vehicle management system 115 to apply weights to subsets of the biometric data, compare the weighted biometric abnormality thresholds, and determine the monitored vehicle 101 has encountered or is currently experiencing a monitored vehicle event representative of Cat. The apparatus 200 may further configure the vehicle management system 115 to provide an indication of the monitored vehicle event, the weighted biometric data, metadata, vehicle data, and/or the like to the apparatus in response to the determination.

In some embodiments, the apparatus 200 (or vehicle management system 115) further determines whether the monitored vehicle 101 has encountered the monitored vehicle event based at least in part on determining that biometric data for a threshold number of subjects (e.g., 2 subjects, 5 subjects, or any suitable number) meets a respective biometric abnormality threshold. In doing so, the apparatus 200 may distinguish between collective biological responses representative of CAT encounters and individualized biological responses that are unassociated with CAT (e.g., said experiences being associated with other factors, such as a personal health event, distress, anxiety, excitement, and/or the like). In some embodiments, the apparatus 200 further determines whether the monitored vehicle encountered the monitored vehicle event based at least in part on a PIREP, vehicle data, weather data, and/or the like. For example, the vehicle management system 115 may automatically generate a PIREP, compensated EDR, and/or the like in response to biometric data meeting a biometric abnormality threshold. The apparatus 200 may receive the PIREP, compensated EDR, and/or the like from the vehicle management system 115 via downlink. The apparatus 200 may determine that the monitored vehicle 101 encountered CAT further based at least in part on processing the PIREP (e.g., to identify indications of turbulence intensity and frequency) and/or comparing the compensated EDR to one or more predetermined thresholds.

At operation 527, the apparatus 200 includes means such as the prediction circuitry 209, the communications circuitry 205, the input/output circuitry 207, the processor 201, and/or the like, or a combination thereof, that generate a predicted event location of the monitored vehicle event representing CAT. For example, the apparatus 200 may generate a predicted event location based at least in part on vehicle data associated with the monitored vehicle 101. In some embodiments, the vehicle data includes one or more vehicle locations, altitudes, speeds, bearings, headings, pitches, EDR, and/or the like. In some embodiments, the apparatus 200 receives vehicle data from the vehicle management system at operation 515. For example, in response to the vehicle management system 115 and/or one or more biometric monitoring devices 104 determining that biometric data meets a respective biometric abnormality threshold, the vehicle management system may provide vehicle data to the apparatus 200. Additionally, the apparatus 200 may receive weather data from one or more environment monitoring systems 106, the monitored vehicle 101, and/or the like. The vehicle management system 115 or apparatus 200 may compensate the vehicle data, weather data, and/or the like based at least in part on the biometric data. For example, the biometric data may include a timestamp indicative of an interval in which one or more subsets of the biometric data met a respective biometric abnormality threshold. The apparatus 200 or vehicle management system 115 may compensate the vehicle data based at least in part on the timestamp to obtain a subset of vehicle data that is associated with the interval.

In some embodiments, the predicted event location includes geographic coordinates and/or the like. For example, the predicted event location may include a longitude and latitude indicative of where the monitored vehicle 101 encountered the monitored vehicle event representing CAT. In some embodiments, the predicted event location includes an altitude, elevation, and/or the like at which the monitored vehicle event was encountered. In some embodiments, the predicted event location includes a timestamp at which the monitored vehicle event was encountered. In some embodiments, the predicted event location includes an intensity, frequency, and/or the like of the CAT. For example, the apparatus 200 may receive a PIREP, EDR, and/or the like from the vehicle management system 115 in response to the biometric data meeting a respective biometric abnormality threshold. The apparatus 200 may determine a CAT frequency, CAT intensity, and/or the like based at least in part on the PIREP. The CAT frequency may include intermittent, occasional, continuous, and/or the like. The CAT intensity may include light, moderate, extreme, severe, and/or the like.

At operation 530, the apparatus 200 includes means such as the prediction circuitry 209, the communications circuitry 205, the input/output circuitry 207, the processor 201, and/or the like, or a combination thereof, that provide the predicted event location to one or more vehicles. For example, the apparatus 200 may provide the predicted event location to the monitored vehicle 101, one or more additional vehicles 105, and/or the like. In doing so, the apparatus 200 may improve awareness of CAT and, as result, improve vehicle safety, subject safety, subject comfort, vehicle performance, and/or the like. In some embodiments, the apparatus 200 embodies a first ground station and provides the predicted event location to one or more additional ground stations. In some embodiments, the apparatus 200 determines one or more vehicles 105 that are within a predetermined range of the predicted event location and provides the predicted event location to the one or more determined vehicles 105. For example, the apparatus 200 may obtain vehicle data for a plurality of vehicles, where the vehicle data includes a current location, travel pathway, and/or the like of a respective vehicle. The apparatus 200 may determine a subset of vehicles that are within a predetermined range of the predicted event location (e.g., 10 miles, 100 miles, or another suitable value) or are predicted to move within the predetermined range based at least in part on the vehicle data. The apparatus 200 may provision the predicted event location (or a modified travel pathway) to the subset of vehicles.

In some embodiments, the apparatus 200 modifies one or more travel pathways for one or more vehicles 105 based at least in part on the predicted event location. For example, the apparatus 200 may modify a travel pathway to circumvent an area comprising the predicted event location to reduce a likelihood of a vehicle encountering CAT. As another example, the apparatus 200 may modify a travel pathway to include an indication of the predicted event location. The predicted event location (or modified travel pathway indicative thereof) may enable a vehicle operator to better navigate through or around the predicted event location. Additionally, or alternatively, the predicted event location may enable the vehicle operator to instruct crewmembers, passengers, maintenance personnel, cargo management personnel, and/or the like to prepare for a potential encounter with CAT. In doing so, the apparatus 200 may improve vehicle safety, passenger and crewmember safety, vehicle efficiency, and/or the like.

CONCLUSION

Although an example processing system has been described above, implementations of the subject matter and the functional operations described herein can be implemented in other types of digital electronic circuitry, or in computer software, firmware, or hardware, including the structures disclosed in this specification and their structural equivalents, or in combinations of one or more of them. Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a repository management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random-access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

In some embodiments, some of the operations above may be modified or further amplified. Furthermore, in some embodiments, additional optional operations may be included. Modifications, amplifications, or additions to the operations above may be performed in any order and in any combination.

Many modifications and other embodiments of the disclosure set forth herein will come to mind to one skilled in the art to which this disclosure pertains having the benefit of the teachings presented in the foregoing description and the associated drawings. Therefore, it is to be understood that the embodiments are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

While this specification contains many specific implementation details, these should not be construed as limitations on the scope of any disclosures or of what may be claimed, but rather as descriptions of features specific to particular embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method, comprising:

receiving, from a vehicle, real-time biometric data for at least one subject aboard the vehicle in response to the real-time biometric data for the at least one subject aboard the vehicle meeting at least one biometric abnormality threshold;

generating a first subset of weighted biometric data at least in part by applying a first weight value to at least a first subset of the real-time biometric data determined to correspond to at least one passenger aboard the vehicle;

generating a second subset of weighted biometric data at least in part by applying a second weight value to at least a second subset of the real-time biometric data determined to correspond to at least one crewmember aboard the vehicle, wherein the first weight value represents a greater impact value than the second weight value;

determining the vehicle has encountered a monitored vehicle event representing clear air turbulence (CAT), wherein the determination that the vehicle has encountered the monitored vehicle event is based at least in part on the first subset of weighted biometric data and the first weight value and the second subset of weighted biometric data and the second weight value;

obtaining vehicle data associated with the vehicle;

generating a predicted event location corresponding to the monitored vehicle event based at least in part on the vehicle data; and providing the predicted event location to at least one additional vehicle.

2. The computer-implemented method of claim 1, further comprising:

configuring the at least one biometric abnormality threshold on at least one of:

a biometric monitoring device carried by the at least one subject aboard the vehicle; or a vehicle management system configured to receive biometric readings from at least one sensor installed within the vehicle, wherein each of the biometric monitoring device or the vehicle management system are configured to generate and analyze the real-time biometric data for the at least one subject based on the at least one biometric abnormality threshold.

3. The computer-implemented method of claim 2, further comprising:

generating the at least one biometric abnormality threshold based at least in part on historical biometric data associated with the at least one subject.

4. The computer-implemented method of claim 1, wherein:

the real-time biometric data comprises at least one of heart rate, respiration rate, pulse, or blood pressure.

5. The computer-implemented method of claim 1, wherein:

the real-time biometric data comprises at least one voice signature.

6. The computer-implemented method of claim 1, wherein:

the real-time biometric data comprises eye movement frequency.

7. The computer-implemented method of claim 1, wherein:

the real-time biometric data comprises at least one blood oxygen level.

8. The computer-implemented method of claim 1, wherein:

the real-time biometric data comprises at least one timestamp for a time interval in which the real-time biometric data met the at least one biometric abnormality threshold.

9. The computer-implemented method of claim 8, wherein:

the vehicle data comprises at least one of a vehicle location, vehicle speed, vehicle pitch, or vehicle altitude measured within the time interval.

10. The computer-implemented method of claim 1, further comprising:

determining the vehicle has encountered the monitored vehicle event representing CAT further based at least in part on a pilot report (PIREP) associated with the vehicle.

11. The computer-implemented method of claim 10, wherein:

the vehicle is configured to generate the PIREP in response to the real-time biometric data meeting the at least one biometric abnormality threshold.

12. The computer-implemented method of claim 1, further comprising:

determining the vehicle has encountered the monitored vehicle event representing CAT further based at least in part on weather data associated with a travel pathway of the vehicle.

13. An apparatus comprising at least one processor and at least one non-transitory memory having computer-coded instructions stored thereon that, in execution with at least one processor, cause the apparatus to:

receive, from a vehicle, real-time biometric data for at least one subject aboard the vehicle in response to the real-time biometric data for the at least one subject aboard the vehicle meeting at least one biometric abnormality threshold;

generate a first subset of weighted biometric data at least in part by application of a first weight value to at least a first subset of the real-time biometric data determined to correspond to at least one passenger aboard the vehicle;

generating a second subset of weighted biometric data at least in part by application of a second weight value to at least a second subset of the real-time biometric data determined to correspond to at least one crewmember aboard the vehicle, wherein the first weight value represents a greater impact value than the second weight value;

determine the vehicle has encountered a monitored vehicle event representing clear air turbulence (CAT), wherein the determination that the vehicle has encountered the monitored vehicle event is based at least in part on the first subset of weighted biometric data and the first weight value and the second subset of weighted biometric data and the second weight value;

obtain vehicle data associated with the vehicle;

generate a predicted event location corresponding to the monitored vehicle event based at least in part on the vehicle data; and provide the predicted event location to at least one additional vehicle.

14. The apparatus of claim 13, wherein:

the real-time biometric data is generated by a biometric monitoring device carried by the at least one subject aboard the vehicle; and the computer-coded instructions, in execution with the at least one processor, further cause the apparatus to:
provision to the biometric monitoring device a request to receive real-time biometric data; and
receive from the biometric monitoring device an approval of the request.

15. The apparatus of claim 13, wherein:

the computer-coded instructions, in execution with the at least one processor, further cause the apparatus to:
receive eddy dissipation rate (EDR) data from the vehicle, wherein the EDR data is compensated based at least in part on a time interval associated with the real-time biometric data.

16. The apparatus of claim 13, wherein:

the at least one biometric abnormality threshold comprises:
a first threshold associated with the at least one passenger; and
a second threshold associated with the at least one crewmember, wherein the second threshold is greater than the first threshold.

17. The apparatus of claim 13, wherein:

the computer-coded instructions, in execution with the at least one processor, further cause the apparatus to:
modify at least one travel pathway based at least in part on the predicted event location.

18. The apparatus of claim 17, wherein:

the computer-coded instructions, in execution with the at least one processor, further cause the apparatus to:
provide the at least one travel pathway to the at least one additional vehicle.

19. The apparatus of claim 18, wherein:

the providing of the at least one travel pathway to the at least one additional vehicle causes the at least one additional vehicle to circumvent an area comprising the predicted event location.

20. A computer program product comprising at least one non-transitory computer-readable storage medium having computer program code stored thereon that, in execution with at least one processor, is configured to:

receive, from a vehicle, real-time biometric data for at least one subject aboard the vehicle in response to the real-time biometric data for the at least one subject aboard the vehicle meeting at least one biometric abnormality threshold;

generate a first subset of weighted biometric data at least in part by application of a first weight value to at least a first subset of the real-time biometric data determined to correspond to at least one passenger aboard the vehicle;

generate a second subset of weighted biometric data at least in part by application of a second weight value to at least a second subset of the real-time biometric data determined to correspond to at least one crewmember aboard the vehicle, wherein the first weight value represents a greater impact value than the second weight value;

determine the vehicle has encountered a monitored vehicle event representing clear air turbulence (CAT), wherein the determination that the vehicle has encountered the monitored vehicle event is based at least in part on the first subset of weighted biometric data and the first weight value and the second subset of weighted biometric data and the second weight value;

obtain vehicle data associated with the vehicle;

generate a predicted event location corresponding to the monitored vehicle event based at least in part on the vehicle data; and provide the predicted event location to at least one additional vehicle.

* * * * *